(12) United States Patent
Bollyky et al.

(10) Patent No.: US 11,278,518 B2
(45) Date of Patent: *Mar. 22, 2022

(54) METHODS OF TREATMENT USING 4-METHYLUMBELLIFERONE AND DERIVATIVES THEREOF

(71) Applicant: The Board of Trustees of the Leland Stanford Junior University, Palo Alto, CA (US)

(72) Inventors: Paul L. Bollyky, Palo Alto, CA (US); Nadine Nagy, Palo Alto, CA (US); Kevin Vincent Grimes, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 410 days.

This patent is subject to a terminal disclaimer.

(21) Appl. No.: 16/418,727

(22) Filed: May 21, 2019

(65) Prior Publication Data
US 2019/0269647 A1 Sep. 5, 2019

Related U.S. Application Data

(63) Continuation-in-part of application No. 15/870,755, filed on Jan. 12, 2018, now Pat. No. 10,370,400.

(60) Provisional application No. 62/674,340, filed on May 21, 2018, provisional application No. 62/446,066, filed on Jan. 13, 2017.

(51) Int. Cl.
*A61K 31/353* (2006.01)
*A61K 31/7048* (2006.01)
*A61P 1/16* (2006.01)

(52) U.S. Cl.
CPC ........ *A61K 31/353* (2013.01); *A61K 31/7048* (2013.01); *A61P 1/16* (2018.01)

(58) Field of Classification Search
None
See application file for complete search history.

(56) References Cited

U.S. PATENT DOCUMENTS

| 6,407,073 | B1 | 6/2002 | Trkovnik et al. | |
|---|---|---|---|---|
| 10,285,976 | B2 | 5/2019 | Bollyky et al. | |
| 10,370,400 | B2 * | 8/2019 | Nagy | A61P 19/02 |
| 2016/0184262 | A1 | 6/2016 | Bollyky et al. | |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596 (Year: 1996).*
Abate, A., et al., "Hymecromone in the Treatment of Motor Disorders of the Bile Ducts: A Multicenter, Double-Blind, Placebo-Controlled Clinical Study," Drugs Under Experimental and Clinical Research 27(5-6):223-231, 2001.
Bollyky, P.L., et al., "4-Methylumbelliferone Treatment for Immune Modulation," U.S. Appl. No. 14/911,533, filed Feb. 11, 2016, 51 pages.
Bollyky, P.L., et al., "CD44 Costimulation Promotes FoxP3+ Regulatory T Cell Persistence and Function via Production of IL-2, IL-10, and TGF-β," Journal of Immunology 183:2232-2241, 2009.
Bollyky, P.L., et al., "Cutting Edge: High Molecular Weight Hyaluronan Promotes the Suppressive Effects of CD4+CD25+Regulatory T Cells," Journal of Immunology 179:744-747, 2007.
Colombaro, V., et al., "Inhibition of Hyaluronan is Protective Against Renal Ischaemia-Reperfusion Injury," Nephrology, Dialysis, Transplanation: Official Publication of the European Dialysis and Transplant Association—European Renal Association 28(10):2484-2493, 2013.
Garrett, E.R., et al., "Pharmacokinetics and Bioavailabilities of Hymecromone in Human Volunteers," Biopharmaceutics & Drug Disposition 14:13-39, 1993.
Kakizaki, I., et al., "A Novel Mechanism for the Inhibition of Hyaluronan Biosynthesis by 4-Methylumbelliferone," Journal of Biological Chemistry 279(32):33281-33289, Aug. 2004.
Kim, W.R., et al., "A Revised Natural History Model for Primary Sclerosing Cholangitis," Mayo Clinic Proceedings 75(7):688-694, Jul. 2000; Calculator tool found at: <http://www.mayoclinic.org/medical-professionals/model-end-stage-liver-disease/revised-natural-history-model-for-primary-sclerosing-chonalgitis>.
Lokeshwar, V.B., et al., "Antitumor Activity of Hyaluronic Acid Synthesis Inhibitor 4-Methylumbelliferone in Prostate Cancer Cells," Cancer Research 70:2613-2623, 2010.
McKallip, R.J., et al., "Treatment With the Hyaluronic Acid Synthesis Inhibitor 4-Methylumbelliferone Suppresses SEB-Induced Lung Inflammation," Toxins 5:1814-1826, 2013.
Nagy, N., et al., "Inhibition of Hyaluronan Synthesis Accelerates Murine Atherosclerosis: Novel Insights Into the Role of Hyaluronan Synthesis," Circulation 122:2313-2322, 2010.
Nakamura, T., et al., "Hyaluronic-Acid-Deficient Extracellular Matrix Induced by Addition of 4-Methylumbelliferone to the Medium of Cultured Human Skin Fibroblasts," Biochemical and Biophysical Research Communications 208(2):470-475, Mar. 1995.
Saito, T., et al., "The Hyaluronan Synthesis Inhibitor 4-Methylumbelliferone Exhibits Antitumor Effects Against Mesenchymal-Like Canine Mammary Tumor Cells," Oncology Letters 5:1068-1074, 2013.
Sawada, N., et al., "Beneficial Effect of 4-Methylumbelliferone Against Bile Duct Ligation-Induced Hepatic Fibrosis in Rats," Hirosaki Medical Journal 66:143-151, 2016.
Xie, Q., et al., "The Performance of Enhanced Liver Fibrosis (ELF) Test for the Staging of Liver Fibrosis: A Meta-Analysis," PLOS ONE 9:4 e92772, 2014, 11 pages.
Yoshihara, S., et al., "A Hyaluronan Synthase Suppressor, 4-Methylumbelliferone, Inhibits Liver Metastasis of Melanoma Cells," FEBS Letters 579:2722-2726, 2005.

(Continued)

*Primary Examiner* — Traviss C McIntosh, III
(74) *Attorney, Agent, or Firm* — Christensen O'Connor Johnson Kindness PLLC

(57) ABSTRACT

4-methylumbelliferone is useful for the treatment of autoimmune diseases, such as primary sclerosing cholangitis (PSC).

10 Claims, 18 Drawing Sheets

(56) References Cited

OTHER PUBLICATIONS

Yoshioka, Y., et al., "Suppression of Hyaluronan Synthesis Alleviates Inflammatory Responses in Murine Arthritis and in Human Rheumatoid Synovial Fibroblasts," Arthritis & Rheumatism 65(5):1160-1170, May 2013.

* cited by examiner

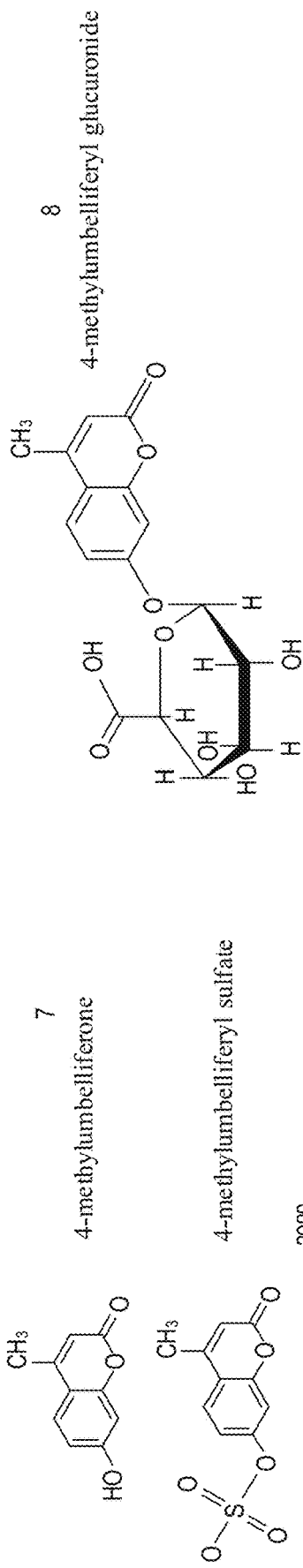
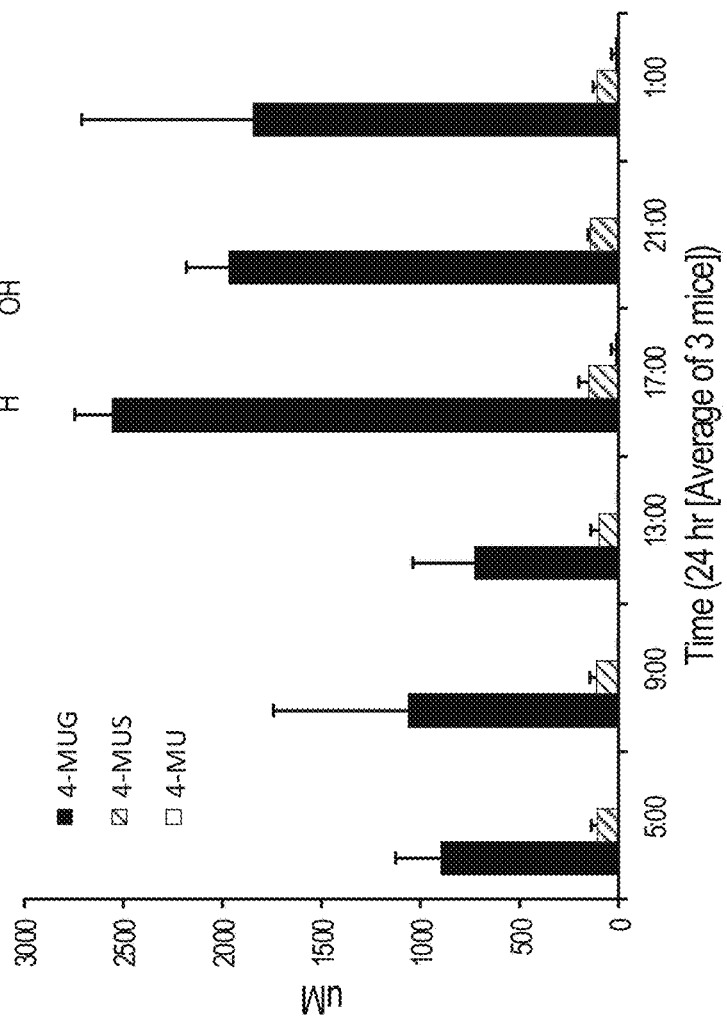
FIG. 1

4-MU derivatives

13 = Ethyl-4-MUG

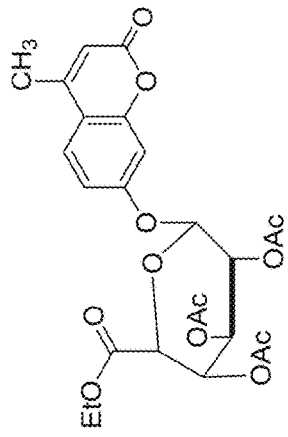

ethyl (2S,3S,4S,5R,6S)-3,4,5-trihydroxy-6-
(((4-methyl-2-oxo-2H-chromen-7-yl)oxy)
tetrahydro-2H-pyran-2-carboxylate
Chemical Formula: C₁₈H₂₀O₉
Molecular Weight: 380.35

14 = Ethyl-4-MUG-Ac

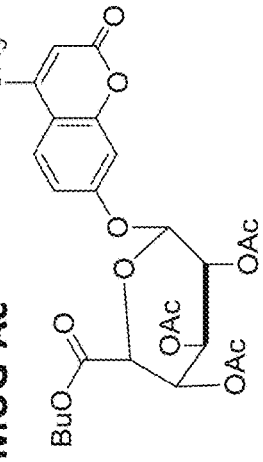

(2S,3S,4S,5R,6S)-2-(ethoxycarbonyl)-6-(((4-methyl-2-oxo-2H-chromen-7-yl)
oxy)tetrahydro-2H-pyran-3,4,5-triyl triacetate
Chemical Formula: C₂₄H₂₆O₁₂
Molecular Weight: 506.46

15 = Butyl-4-MUG

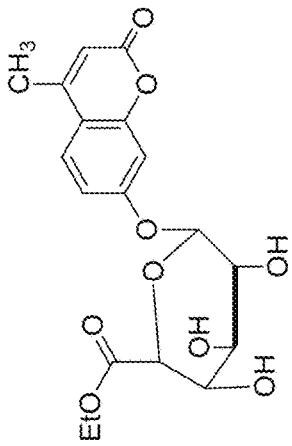

butyl (2S,3S,4S,5R,6S)-3,4,5-trihydroxy-6-
(((4-methyl-2-oxo-2H-chromen-7-yl)oxy)
tetrahydro-2H-pyran-2-carboxylate
Chemical Formula: C₂₀H₂₄O₉
Molecular Weight: 408.40

16 = Butyl-4-MUG-Ac

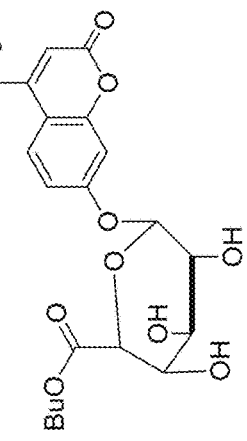

(2S,3S,4S,5R,6S)-2-(butoxycarbonyl)-6-
(((4-methyl-2-oxo-2H-chromen-7-yl)oxy)
tetrahydro-2H-pyran-3,4,5-triyl triacetate
Chemical Formula: C₂₆H₃₀O₁₂
Molecular Weight: 534.51

*FIG. 2*

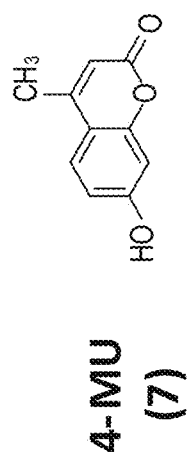
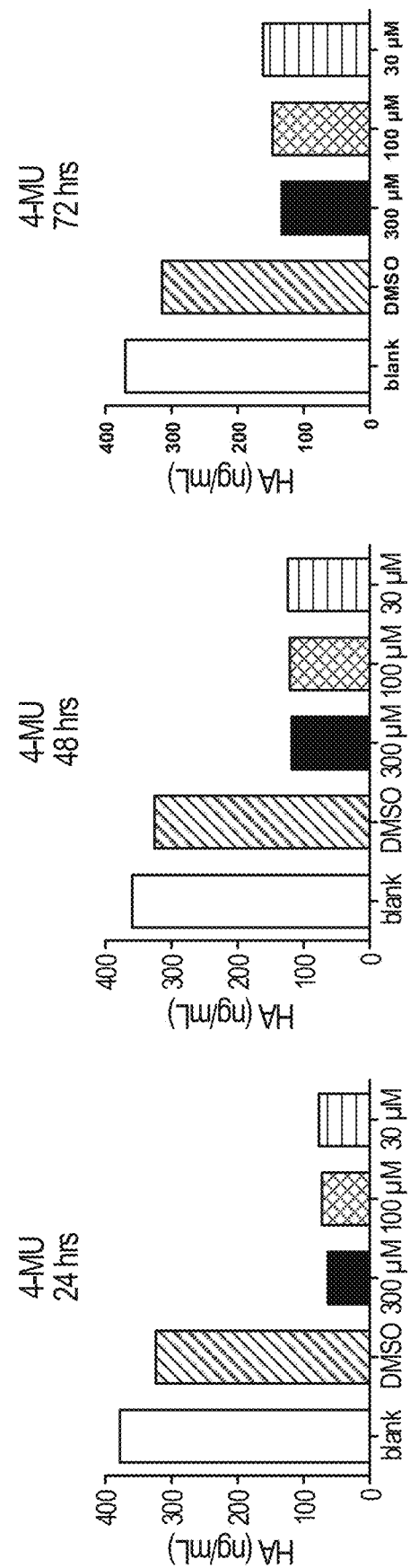
FIG. 3

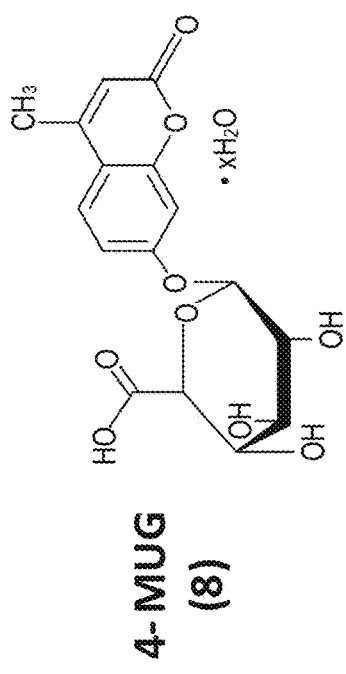
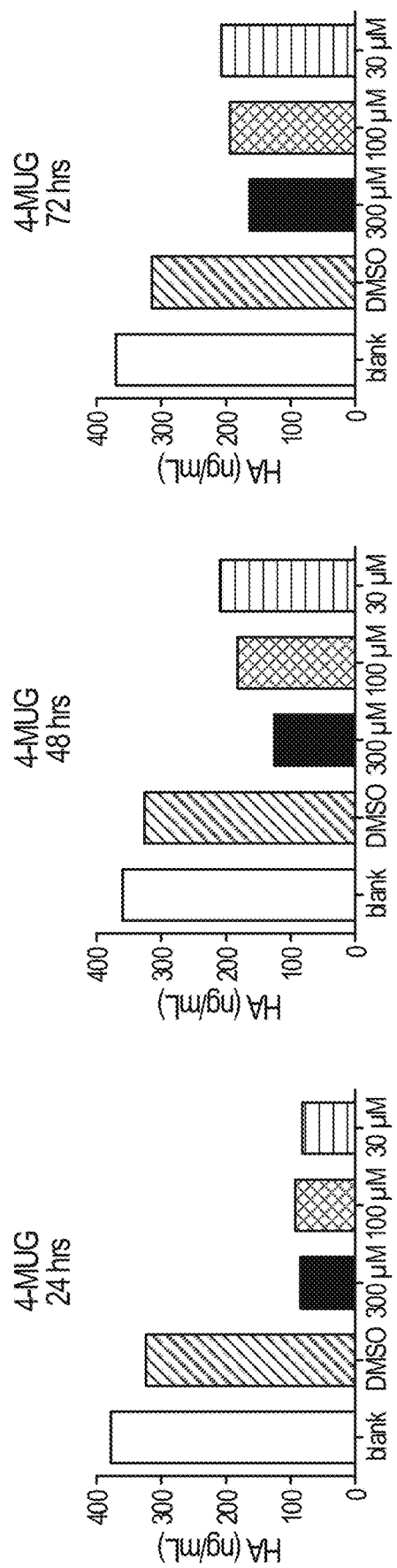
FIG. 4

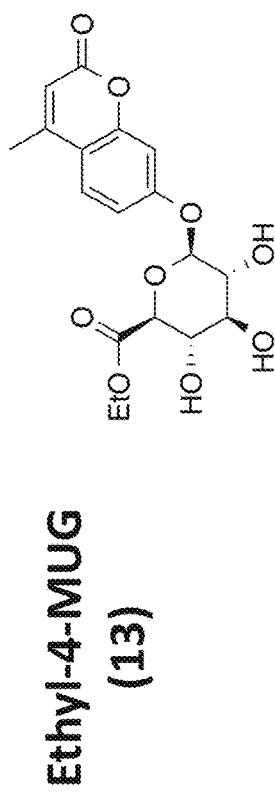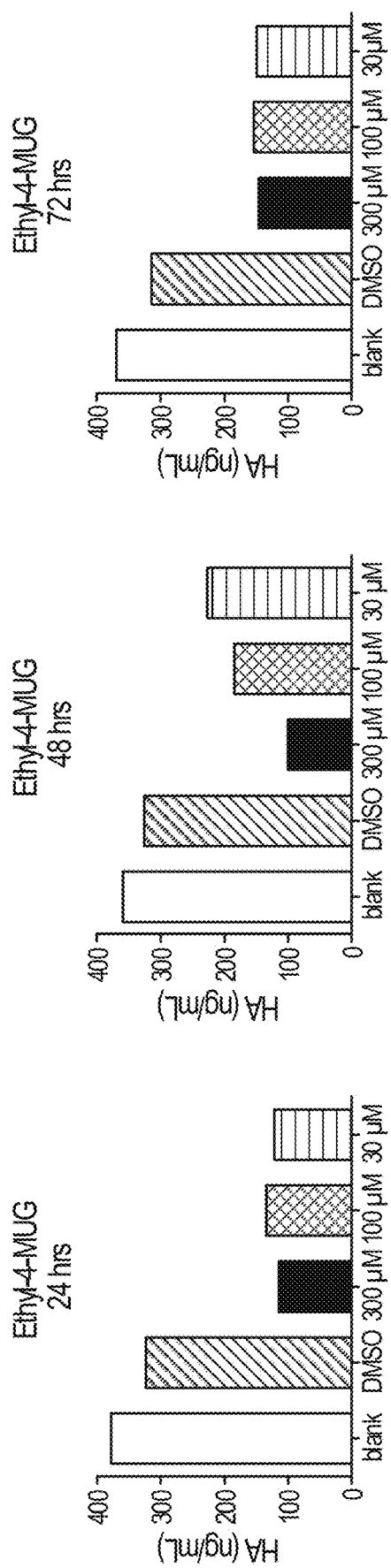
FIG. 5

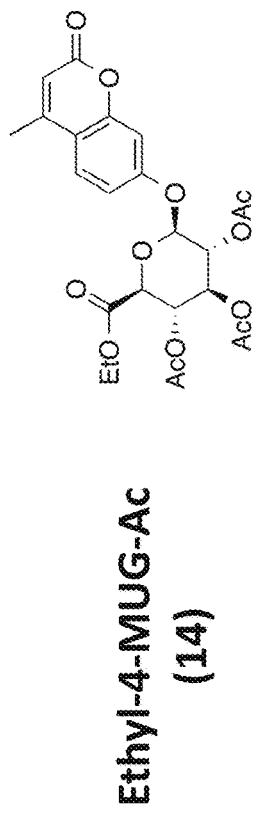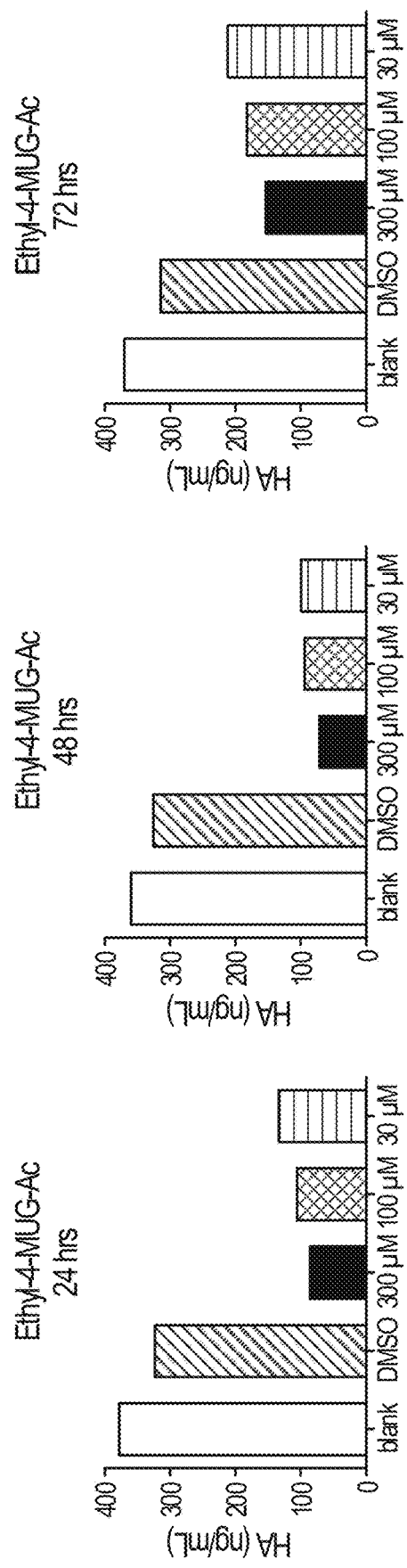
FIG. 6

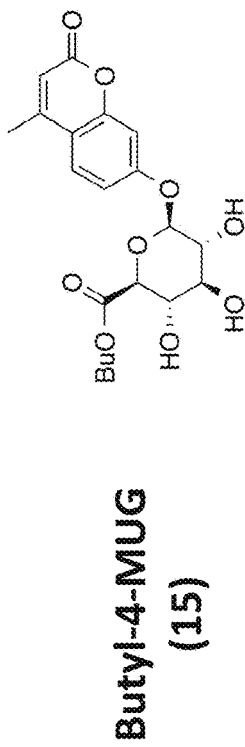
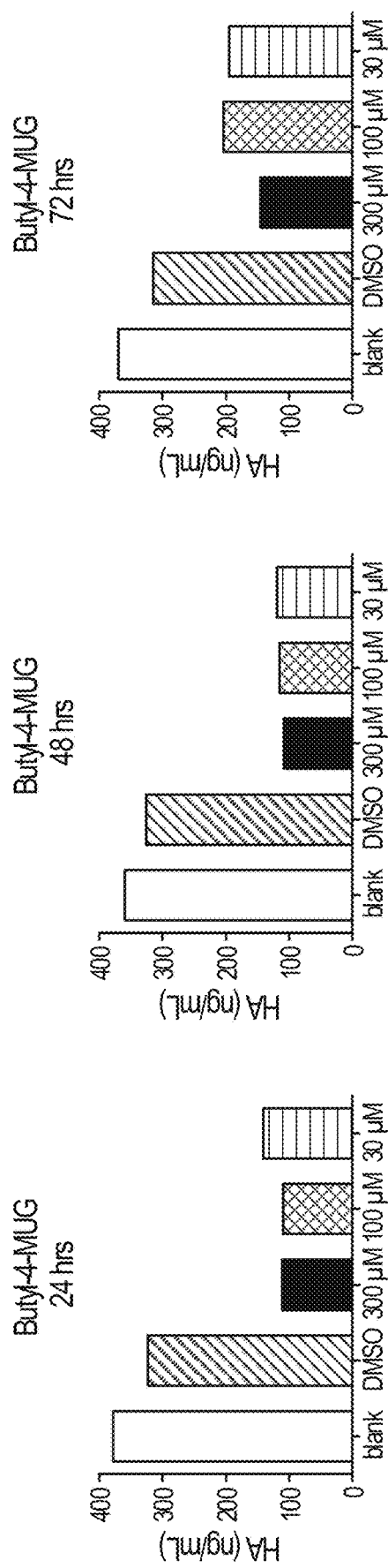
FIG. 7

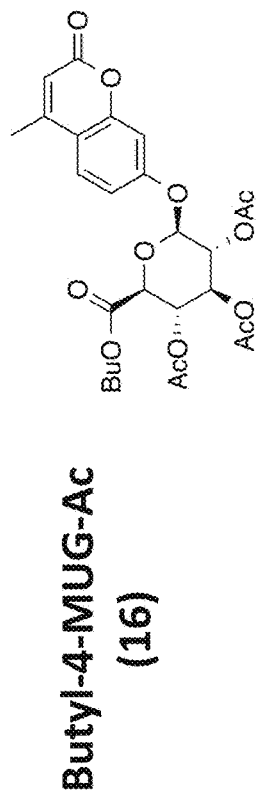
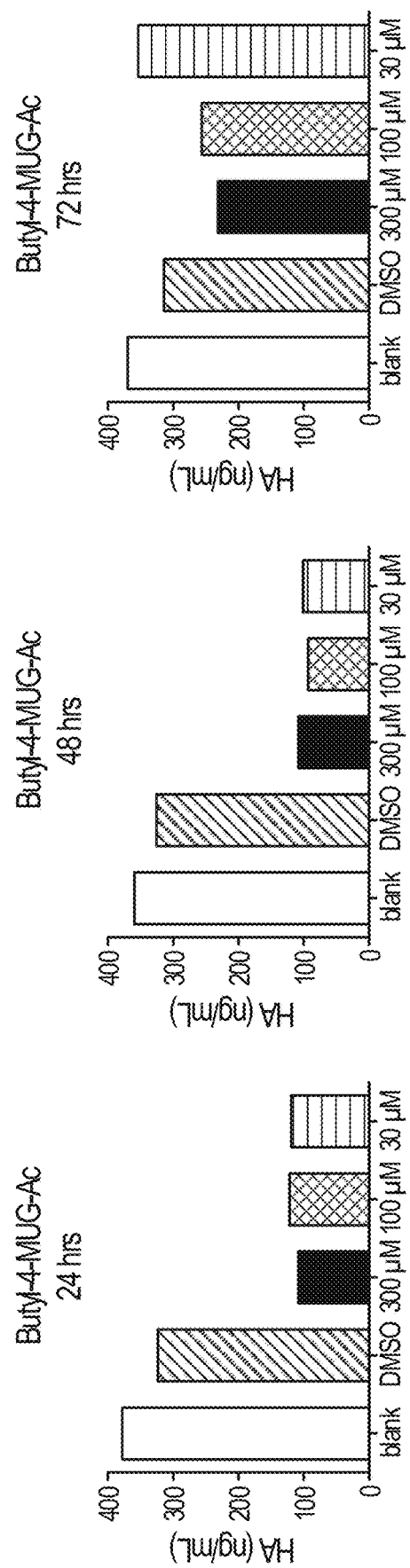
FIG. 8

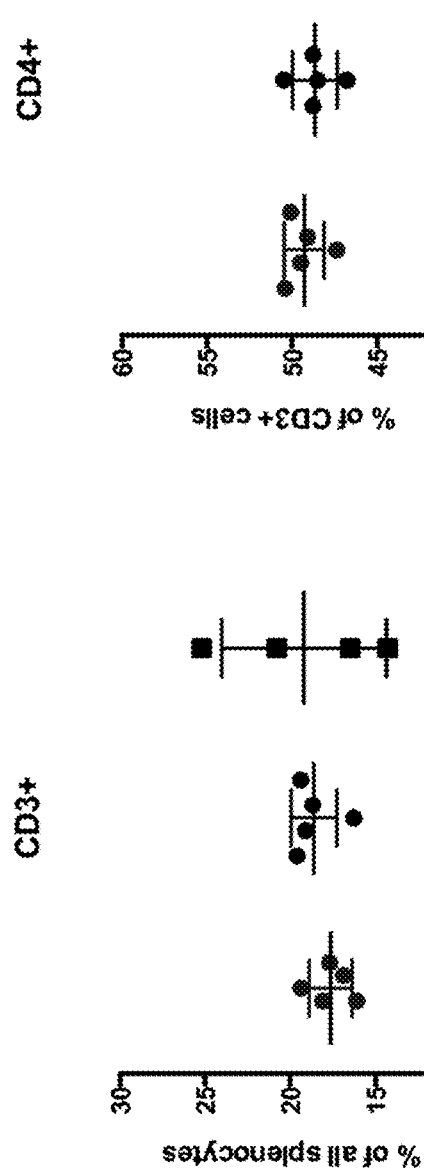
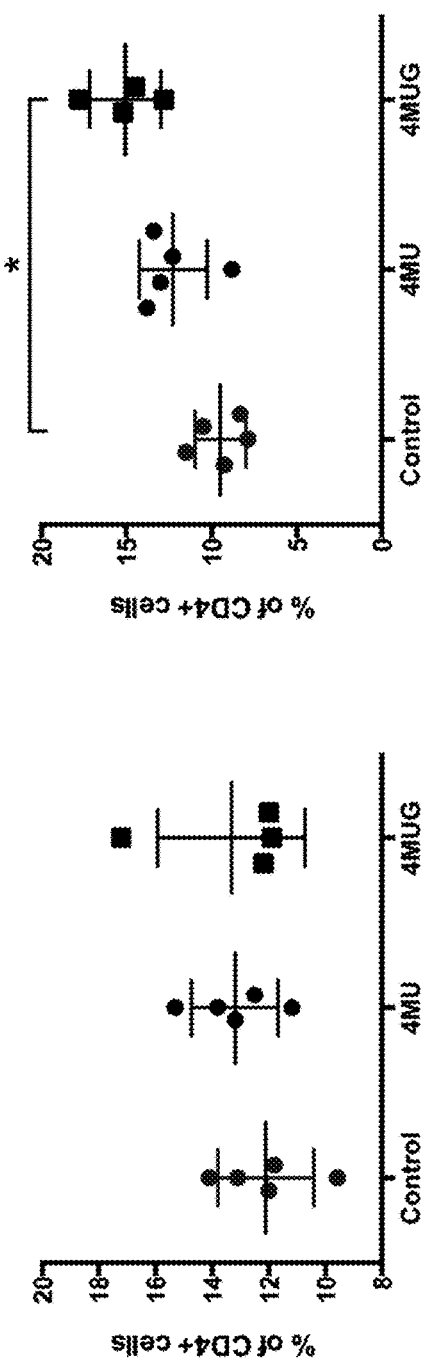
FIG. 11A  FIG. 11B  FIG. 11C  FIG. 11D

METHODS OF TREATMENT USING 4-METHYLUMBELLIFERONE AND DERIVATIVES THEREOF

CROSS-REFERENCES TO RELATED APPLICATIONS

This application claims the benefit of U.S. patent application No. 62/674,340, filed May 21, 2018, and is also a continuation-in-part application of U.S. patent application Ser. No. 15/870,755, filed Jan. 12, 2018, now U.S. Pat. No. 10,370,400, which claims the benefit of U.S. patent application No. 62/446,066, filed Jan. 13, 2017, the disclosure of each of which is incorporated herein by reference in its entirety.

STATEMENT OF GOVERNMENT LICENSE RIGHTS

This invention was made with Government support under R01 DK096087-07, U01 AI101984, and R01 DK114174-01A1 awarded by the National Institutes of Health (NIH). The Government has certain rights in the invention.

FIELD OF THE INVENTION

The present disclosure relates to immunomodulatory compositions and methods of using the compositions to inhibit hyaluronan synthesis. The disclosure also relates to compositions and methods for treating an autoimmune disease or inflammatory disorder such as diabetes, multiple sclerosis, and primary sclerosing cholangitis.

BACKGROUND

Hyaluronan (HA) is an extracellular matrix (ECM) glycosaminoglycan (GAG), which has many roles in normal tissue function and development. This includes providing support and anchorage for cells, facilitating cell-cell signaling, and facilitating cell movement and migration (Jiang D., et al., *Annu. Rev. Cell Dev. Biol.*, 23, 435-461 (2007); Jiang, D., Liang, J. and Noble, P. W., *Physiol. Rev.* 91, 221-264 (2011); Laurent T. C., et al., *Immunol. Cell Biol.* 74, A1-7 (1996)). HA interacts with a complex network of ECM molecules that together exert decisive effects on the physical and immunologic properties of inflamed tissues (Bollyky, P. L., et al., *Curr. Diab. Rep.* 12, 471-480 (2012); Hull, R. L., et al., *J. Histochem. Cytochem.* 60, 749-760 (2012); Bogdani, M. et al., *Diabetes* 63, 2727-2743 (2014); Bogdani, M. et al., *Curr. Diab. Rep.* 14, 552-11 (2014)). In light of its central role in this network, it is believed that HA is a "keystone molecule" in the inflammatory milieu (Bollyky, P. L., et al., *Curr. Diab. Rep.* 12, 471-480 (2012)).

HA is a polymer of disaccharides composed of glucuronic acid and N-acetylglucosamine and linked via alternating β-1, 4 and β-1, 3 glycosidic bonds. HA can be about 25,000 disaccharide repeats in length. In vivo polymers of HA can range in size from 5,000 to 20,000,000 Da. HA is synthesized by a class of integral membrane proteins called HA synthases, of which vertebrates have three types: HAS1, HAS2, and HAS3. These enzymes lengthen HA by repeatedly adding glucuronic acid and N-acetylglucosamine to the nascent polysaccharide as it is extruded through the cell membrane into the extracellular space.

HA synthesis increases substantially at sites of inflammation (Laurent, T. C., et al., Immunol. Cell Biol. 74, A1-7 (1996)), with HA production increasing by as much as 80-fold (Laurent T. C., et al., *Immunol. Cell Biol.* 74, A1-7 (1996)). Increases in HA are associated with many chronic disease processes with unremitting inflammation, including type 2 diabetes (T2D) (Mine, S., et al., *Endocr.* 1 53, 761-766 (2006); Kang, L. et al., *Diabetes* 62, 1888-1896 (2013)), liver cirrhosis, asthma, and other chronic inflammatory diseases of diverse etiologies (Plevris, J. N. et al., *Eur. J Gastroenterol. Hepatol.* 12, 1121-1127 (2000); Wells, A. F. et al., *Transplantation* 50, 240-243 (1990); Dahl, L. B., et al., *Ann. Rheum. Dis.* 44, 817-822 (1985); Hällgren, R., et al., *Am. Rev. Respir. Dis.* 139, 682-687 (1989); Evanko, S. P., et al., *Am. J. Pathol.* 152, 533-546 (1998); Cheng, G. et al., *Matrix Biol.* 30, 126-134 (2011); Ayars, A. G. et al., *Int. Arch. Allergy Immunol.* 161, 65-73 (2013); Liang, J. et al., *J. Allergy Clin. Immunol.* 128, 403-411.e3 (2011)). HA has been implicated in multiple autoimmune diseases including rheumatoid arthritis (Yoshioka Y, et al., *Arthritis Rheum.* 65, 1160-1170 (2013), lupus (Yung S., et al., *Hindawi* 2012, 207190-9 (2012)), and Hashimotos's thyroiditis (Shan, S. J. C. & Douglas, R. S., *J Neuroophthalmol.* 34, 177-185 (2014)). HA surrounds tumors in diverse forms of cancer (Toole, B. P., *Nat. Rev. Cancer* 4, 528-539 (2004)), this accumulation of HA is part of a larger pattern of ECM deposition associated with persistent inflammation.

HA increases local edema (Waldenström, A., et al., *J. Clin. Invest.* 88, 1622-1628 (1991) and contributes to an inflammatory cascade that drives leukocyte migration, proliferation, differentiation through effects on gene expression and cytokine production and cell survival. These pathways and the impact of HA production on innate immunity are the subject of several excellent reviews (Jiang D., et al., *Annu. Rev. Cell Dev. Biol.*, 23, 435-461 (2007); Jiang, D., Liang, J. and Noble, P. W., *Physiol. Rev.* 91, 221-264 (2011); Petrey, A. C. and la Motte, de, C. A., *Front Immunol.* 5, 101 (2014); Slevin, M. et al., *Matrix Biol.* 26, 58-68 (2007); Sorokin, L., *Nat. Rev. Immunol.* 10, 712-723 (2010)).

Catabolic, low-molecular weight fragments of HA (LMW-HA) act as endogenous danger signals that promote antigenic responses (Termeer, C. et al., *J. Exp. Med.* 195, 99-111 (2002) and immune activation (Jiang, D., Liang, J. and Noble, P. W., *Physiol. Rev.* 91, 221-264 (2011) via CD44 and Toll-like receptor (TLR) signaling (Jiang, D. et al., *Nat. Med.* 11, 1173-1179 (2005); Fieber, C. et al., *J. Cell. Sci.* 117, 359-367 (2004); Termeer, C., et al., *Trends Immunol.* 24, 112-114 (2003); Taylor, K. R. et al., *J. Biol. Chem.* 279, 17079-17084 (2004)). LMW-HA also promotes the activation and maturation of dendritic cells (DC) (Termeer, C. et al., *J. Exp. Med.* 195, 99-111 (2002)), drives the release of pro-inflammatory cytokines such as IL-1ß, TNF-alpha, IL-6 and IL-12 by multiple cell types (Bollyky, P. L. et al., *J. Immunol.* 179, 744-747 (2007); Bollyky, P. L. et al., *Proc. Natl. Acad. Sci. U.S.A.* 108, 7938-7943 (2011)), drives chemokine expression and cell trafficking (McKee, C. M. et al., *J. Clin. Invest.* 98, 2403-2413 (1996)), and promotes proliferation (Scheibner, K. A. et al., *J. Immunol.* 177, 1272-1281 (2006)).

Autoimmune Diseases

An autoimmune disease or disorder occurs when the body's immune system attacks and destroys healthy body tissue by mistake. Autoimmune diseases can attack almost any tissue in the body and all autoimmune diseases are characterized by local inflammation and infiltration by immune cells called lymphocytes.

As an example, autoimmune diabetes, also known as type 1 diabetes (T1D) or insulin-dependent diabetes mellitus (IDDM), occurs when the body's immune system mistakenly destroys the pancreatic cells, called beta cells, which make insulin. Damage to beta cells results in an absence or insufficient production of insulin produced by the body. In all autoimmune diseases, including autoimmune diabetes, lymphocytes migrate from the blood stream into target tissues via interactions with the extracellular matrix. In the case of autoimmune diabetes, lymphocytes attack pancreatic islets via interaction with extracellular matrix that lies between islet capillaries and endocrine cells.

One in three hundred American children will develop autoimmune diabetes. Many of these individuals can be identified before they present with hyperglycemia through screening for autoimmune diabetes associated autoantibodies. Thus, there is a therapeutic window where autoimmune diabetes could be prevented, given the knowledge and means to do so. The present disclosure describes novel strategies to reverse, ameliorate, and/or prevent the progression to autoimmune diabetes in at-risk individuals.

As an example, multiple sclerosis (MS) is also an autoimmune disease but in MS the autoimmune activity is directed against central nervous system (CNS) antigens. The disease is characterized by inflammation in parts of the CNS, leading to the loss of the myelin sheathing around neuronal axons (demyelination), axonal loss, and the eventual death of neurons, oligodendrocytes and glial cells. For a comprehensive review of MS and current therapies, see, e.g., Compston, A., et al., *McAlpine's Multiple Sclerosis* 4th ed., Churchill Livingstone Elsevier (2006).

MS is one of the most common diseases of the CNS in young adults, and an estimated 2.5 million people suffer from MS. MS is a chronic, progressing, disabling disease, which generally strikes its victims sometime after adolescence, with diagnosis generally made between 20 and 40 years of age, although onset can occur earlier. The disease is not directly hereditary, although genetic susceptibility plays a part in its development. MS is a complex disease with heterogeneous clinical, pathological and immunological phenotype.

There are four major clinical types of MS: 1) relapsing-remitting MS (RRMS), characterized by clearly defined relapses with full recovery or with sequelae and residual deficit upon recovery; periods between disease relapses are characterized by a lack of disease progression; 2) secondary progressive MS (SPMS), characterized by an initial relapsing remitting course followed by progression with or without occasional relapses, minor remissions, and plateaus; 3) primary progressive MS (PPMS), characterized by disease progression from onset with occasional plateaus and temporary minor improvements allowed; and 4) progressive relapsing MS (PRMS), characterized by progressive disease onset, with clear acute relapses, with or without full recovery; periods between relapses characterized by continuing progression.

Clinically, the illness most often presents as a relapsing-remitting disease and, to a lesser extent, as steady progression of neurological disability. Relapsing-remitting MS presents in the form of recurrent attacks of focal or multifocal neurologic dysfunction. Attacks can occur, remit, and recur, seemingly randomly over many years. Remission is often incomplete and as one attack follows another, a stepwise downward progression ensues with increasing permanent neurological deficit. The usual course of RRMS is characterized by repeated relapses associated, for the majority of patients, with the eventual onset of disease progression. The subsequent course of the disease is unpredictable, although most patients with a relapsing-remitting disease will eventually develop secondary progressive disease. In the relapsing-remitting phase, relapses alternate with periods of clinical inactivity and may or may not be marked by sequelae depending on the presence of neurological deficits between episodes. Periods between relapses during the relapsing-remitting phase are clinically stable. On the other hand, patients with progressive MS exhibit a steady increase in deficits as defined above and either from onset or after a period of episodes, but this designation does not preclude the further occurrence of new relapses.

In healthy individuals (i.e., those without an autoimmune disease or disorder), immune tolerance is maintained by populations of regulatory T-cells including FoxP3+ regulatory T-cells (Treg) (Sakaguchi, S., et al., *Nat. Rev. Immunol.* 10, 490-500 (2010)). Treg absence or depletion leads to multi-systemic autoimmunity, including autoimmune diabetes, in mice and humans (Wildin, R. S., et al., *Nat. Genet.* 27, 18-20 (2001)) whereas adoptive transfer of Treg can abrogate autoimmunity. In MS, Treg present in the CNS are known to limit the extent of neuroinflammation and to facilitate clinical recovery during the mouse model of multiple sclerosis, experimental autoimmune encephalomyelitis (EAE), such that multiple investigative therapeutic strategies to treat autoimmune demyelination are directed at promoting the number and/or function of Treg.

There is a need for developing tools to induce Foxp3+ Treg because of their ability to suppress inflammation, including autoimmunity (Sakaguchi, S., et al., *Nat. Rev. Immunol.* 10, 490-500 (2010)) but also other inflammatory diseases, including T2D (Eller, K. et al., *Diabetes* 60, 2954-2962 (2011)). However, existing therapies have not managed to induce stable, functional FoxP3+ Treg. This is in part because Treg in vivo are a population in flux. Natural Treg (nTreg) continually emerge through thymic selection, whereas induced Treg (iTreg) originate in peripheral tissues in response to inflammatory stimuli and can revert into effector T-cells. This variability in the number and function of local Treg at sites of inflammation can impact the durability of immune tolerance in peripheral tissues.

Despite the fact that the inflammatory milieu is known to have decisive effects on immune tolerance, little is known about how the tissue micro-environment influences the function and number of Treg. Therefore, there is increasing interest in the role of ECM at the interface between lymphocytes and local cells in autoimmunity (Bollyky, P. L., et al., *Curr. Diab. Rep.* 12, 471-480 (2012); Hull, R. L., et al., *J. Histochem. Cytochem.* 60, 749-760 (2012); Irving-Rodgers, H. F. et al., *Diabetologia* 51, 1680-1688 (2008); Ziolkowski, A. F., et al., *J. Clin. Invest.* 122, 132-141 (2012)).

Primary Sclerosing Cholangitis

Primary sclerosing cholangitis (PSC) is a disease that damages and blocks bile ducts inside and outside the liver. PSC damages the hepatic, cystic, and common bile ducts, which carry bile out of the liver. In PSC, inflammation of the bile ducts (cholangitis) leads to scar formation and hardening (sclerosis), and narrowing of the ducts over time. As scarring increases, the ducts become blocked. As a result, bile builds up in the liver and damages liver cells. Eventually, scar tissue can spread throughout the liver, causing cirrhosis and liver failure.

PSC is a chronic, progressive autoimmune disease of the liver characterized by inflammation, fibrosis, and obliteration of the intra- and extra-hepatic bile ducts. For patients with PSC, an idiopathic immune-mediated inflammation response is mounted on their bile ducts. Over time this leads to biliary obstruction, hepatic fibrosis, portal hypertension, cirrhosis and eventually liver failure. See, e.g., FIG. 15. The only recourse for patients with advanced PSC is liver transplant. Unfortunately, 15-20% of patients with PSC also contract cholangiocarcinoma (cancer in the bile ducts). This is a particularly damning outcome as there are no good screening techniques, nor treatments, for cholangiocarcinoma. Sadly, presence of this cancer is also a contraindication for liver transplant. PSC affects about 35,000 people in the US population (point prevalence of 8.5-13.6 per 100,000) with a similar number of patients suffering from the disease in the EU and about a third as many patients in Japan. The prevalence appears to be rising in developed nations for unknown reasons.

Four clinical phases in the natural history of PSC include 1) Asymptomatic; 2) Biochemical; 3) Symptomatic; and 4) Decompensated.

A patient may be asymptomatic in the early stages of the disease, i.e., there may be no signs or symptoms. As the disease progresses the first sign of trouble typically occurs at the biochemical level. In PSC, a patient's own immune system systematically attacks the epithelium of the bile duct system. Unsurprisingly, constant injury to the epithelium leads to biliary dysfunction. As the epithelial cells of the biliary tract begin to die from the chronic inflammatory response, fibrosis ensues. Strictures began to form (FIGS. 14A and 14B), physically obstructing the flow of bile (cholestasis). This cholestasis has a cumulative, deleterious, and exacerbating effect. Bile acids are predominantly hydrophobic and their pooling in the biliary ducts further weakens the membranes of the epithelial cells. In effect, the underlying autoimmune attack coupled with the concomitant cholestasis is a one-two punch on the epithelium.

In the next phase, as the epithelial cells succumb to this knock-out blow, a biochemical response can be detected: a rise in hepatic enzymes and bilirubin in the blood stream. These are markers for hepatic damage. The first signals are a rise in serum transaminase levels: AST (aspartate aminotransferase) and ALT (alanine aminotransferase) and ALP (alkaline phosphatase). This is followed by a rise in bilirubin. A reduction of hepatic damage or a reduction of the progression of hepatic damage is measured by a reduction in serum levels of ALP, AST, ALT, gamma-glutamyl transferase (GGT) or bilirubin.

In the symptomatic phase, the first clinical signs that a patient will notice are typical those related to cholestasis: namely fatigue, jaundice, and pruritus (caused by bile acid build up in the skin). The severity of these symptoms is variable both for an individual patient and among different patients.

In the decompensated phase, over time, however, liver damage accumulates for all patients. Spreading fibrosis eventually leads to portal hypertension which only serves to spread the fibrotic response.

The median survival post-diagnosis is 12-13 years and their clinical course almost invariably involves needing a liver transplant due to liver failure.

Another closely related condition is primary biliary cholangitis (PBC), previously called primary biliary cirrhosis. Despite sharing common symptoms with PSC such as itching and fatigue, PSC and PBC are distinct entities and exhibit important differences, including the site of tissue damage within the liver, associations with inflammatory bowel disease (IBD), which includes ulcerative colitis and Crohn's disease, response to treatment, and risks of disease progression.

In PSC, a key feature is the development of scar tissue (fibrosis) that predominantly affects the medium- to large-sized bile ducts within and outside the liver. This can most often be identified with a special MRI scan (called MRCP) of the bile ducts, although occasionally a liver biopsy is needed for confirmation. PSC can affect men and women at any age, although it is commonly diagnosed in the fourth decade of life, most often in the presence of inflammatory bowel disease (IBD).

Close monitoring of PSC patients is vital. Because of the increased colon cancer risk in PSC patients with ulcerative colitis, annual colonoscopies are advised. Moreover, the presence of colitis is associated with a greater risk of liver disease progression and bile duct cancer (cholangiocarcinoma). Individuals with PSC can occasionally develop abdominal pain and fever, which may suggest infection of the bile ducts called cholangitis. Although the latter can be treated with antibiotics, no currently known treatment has been shown to slow the progression or cure PSC.

By contrast, PBC mainly affects the small bile ducts in the liver itself and is not associated with biliary sclerosis. In the current era, PBC can be identified through special antibody tests (performed on blood sampling, such as raised ALP and positive disease specific antibodies (or AMA) and liver biopsy is rarely needed. Over 90% of individuals with PBC are women, and the condition is most often diagnosed in middle age via a series of blood tests. Approximately two-thirds of patients with PBC can improve their liver blood tests while taking ursodeoxycholic acid (UDCA), and it is well recognized that this correlates with improved survival and a lower risk of liver transplantation. UDCA has not been proven to slow PSC disease progression. Unlike PSC, PBC does not share an association with IBD, colonic cancer or bile duct cancer; however individuals with PBC can occasionally develop thyroid problems, dry eyes (a condition called Sicca syndrome or Sjögren's syndrome) or intolerance to gluten in wheat (coeliac disease). Also, unlike PSC, PBC is often associated with a history of smoking.

It is important to recognize that PBC and PSC are different diseases; stemming from the way they are diagnosed, the association with IBD, and the way they are monitored and respond to treatment.

Existing Treatment of PSC

Currently there are no approved drugs for PSC. No drug has ever been proven to slow the clinical progression of PSC, although many drugs have been studied (including many antibiotics, heavy duty immuno-suppressants and some anti-fibrotic agents). A partial list of drugs tested for PBC with no proven benefit include: a panoply of antibiotics, Cholestyramine, Corticosteroids, Azathioprine, Methotrexate, Cyclosporine, Tacrolimus, Pentoxifylline, Colchicine, D-penicillamine, Nicotine, Perfenidone, and Mycophenolate Mofetil.

Despite a lack of proven clinical benefit, ursodeoxycholic acid (UDCA; ursodiol; Actigall) is commonly used by clinicians anyway. UDCA is a bile acid that makes up 2-5% of the total bile composition in normal subjects. Upon treatment with UDCA, the composition of biliary fluids is shifted significantly in favor of UDCA such that after only 6 months of treatment a bile concentration of up to 70% can be attained. The compound is well-tolerated with nominal, low-grade diarrhea listed as the most commonly listed adverse event.

The thought process behind the clinical use of UDCA is as follows. Because it is relatively hydrophilic, UDCA's chemical properties make it less toxic to the biliary duct epithelium than other more prevalent bile acids. In this way UDCA is thought to be hepatoprotective. UDCA is known to increase secretion of bile acids and to increase bile flow. Thus, it should help alleviate cholestasis, which is not only the root cause of much of the early clinical symptoms of PSC, but also serves as a driving factor in the progression of the disease. There is also somewhat weak evidence that UDCA is immuno-modulatory. It is not known if this is primary or secondary, nor what the effect on the progression of the disease this may have. While there have been hints of UDCA clinical benefit across multiple clinical trials, none has been statistically proven. In fact, the most rigorous of studies on the compound was halted for futility: see Rupp et al., *Aliment Pharmacol Ther.* 40(11-12): 1292-301 (2014).

HA in Autoimmune and Inflammatory Diseases.

As discussed above, one tissue component that is abundant at sites of inflammation is hyaluronan (HA), an extracellular matrix (ECM) polysaccharide. HA has many functions, such as providing support and anchorage for cells, segregating tissues from one another, facilitating cell to cell signaling, development, migration and function (Bollyky, P. L., et al. (2012), supra). HA is synthesized by a class of integral membrane proteins called hyaluronan synthases and extruded through the cell membrane into the extracellular space (Laurent, T. C., et al., *Immunol. Cell Biol.* 74, A1-7 (1996)).

HA is a key mediator of inflammation, with roles in lymphocyte trafficking, proliferation, and antigen presentation (Laurent, T. C., and Fraser, J. R., FASEB 1 6, 2397-2404 (1992); Bollyky, P. L., et al., *Cell Mol Immunol.* 3, 211-220 (2010)). HA is increased in lesions associated with human autoimmune diseases, including multiple sclerosis, Sjögrens disease, and Graves' Disease (Back, S. A., et al., *Nat. Med.* 11, 966-972 (2005); Engström-Laurent, A. "Changes in hyaluronan concentration in tissues and body fluids in disease states." *The Biology of Hyaluronan*, CIBA Foundation Symposium, 143, 233-47 (1989); Gianoukakis, A., et al., *Endocrinology* 148, 54-62 (2007). HA is also increased in the serum of individuals with Lupus, rheumatoid arthritis, psoriasis, and autoimmune thyroiditis (Engström-Laurent, supra; Pitsillides et al., *Rheumatol.* 33, 5-10 (1994); Hansen, C., et al., *Clin. Exp. Rheumatol.* 14 Suppl. 15, S59-67 (1996); Torsteinsdottir et al., *Clin. Exp. Immunol.* 115, 554-560 (1999); Elkayam, O., et al., *Clin. Rheumatol.* 19, 455-457 (2000); Kubo, M., et al., *Arch. Dermatol. Res.* 290, 579-581 (1998).

HA is produced by a variety of cell types in response to inflammatory stimuli including hyperglycemia (Shakya, S., et al., *Int. J. Cell Biol.* 2015, 701738-11 (2015); Wang, A. and Hascall, V. C., *Autophagy* 5, 864-865 (2009)), inflammatory cytokines (Bollyky, P. L. et al., *Cell. Mol. Immunol.* 7, 211-220 (2010)), and other triggers (Lauer, M. E. et al., *J. Biol. Chem.* 284, 5299-5312 (2009)). The HA present within inflamed tissues functions as an endogenous "danger signal" (Noble, P. W., *Matrix Biol.* 21, 25-29 (2002)) and promotes inflammatory responses (Jiang, D., Liang, J. and Noble, P. W., *Physiol. Rev.* 91, 221-264 (2011); la Motte, de, C. et al., *Am. J. Pathol.* 174, 2254-2264 (2009)).

HA is highly abundant within chronically inflamed tissues including for example MS lesions (Back, S. A. et al., *Nat. Med.* 11, 966-972 (2005)). For example, in one study HA was shown to accumulate in demyelinated lesions in MS and EAE. Immunostaining for proteolipid protein (PLP) of a chronic MS lesion showed complete loss of myelin in the center of the lesions. CD44 staining revealed high levels of CD44 in the lesions, and elevated CD44 expression in GFAP-expressing reactive astrocytes were also found. HA staining showed high levels of HA in demyelinated regions of the lesions but at lower levels in the lesion borders (Back, S. A. et al., *Nat. Med.* 11, 966-972 (2005)).

Typically, HA present within chronically inflamed tissues takes the form of short, highly catabolized fragments (as reviewed in Bollyky, P. L., et al., *Curr. Diab. Rep.* 12, 471-480 (2012)) that are pro-inflammatory agonists of Toll-like receptor signalling (Jiang, D., Liang, J. and Noble, P. W., *Physiol. Rev.* 91, 221-264 (2011); Laurent, T. C., et al., *Immunol. Cell Biol.* 74, A1-7 (1996)), driving dendritic cell maturation, and promoting phagocytosis (Termeer, C. et al., *J. Exp. Med.* 195, 99-111 (2002); Jiang, D. et al., *Nat. Med.* 11, 1173-1179 (2005)). HA overexpression tends to drive inflammation (Olsson, M., et al., PLOS Genetics 7, e1001332 (2011)) presumably through production of increased HA fragments, while inhibition of HA synthesis, including treatment with 4-methylumbelliferone (4-MU, Hymecromone), tends to reduce inflammation (Yoshioka, Y. et al., *Arthritis Rheum.* 65, 1160-1170 (2013); McKallip, R. J., et al., *Inflammation* 38, 1250-1259 (2015); Colombaro, V. et al., *Nephrol. Dial. Transplant.* 28, 2484-2493 (2013)). With respect to the role of HA in local immune modulation, it is known that low molecular weight HA fragments inhibit the function of FoxP3+ Treg (Bollyky, P. L. et al., *J. Immunol.* 179, 744-747 (2007); Bollyky, P. L. et al., *J. Immunol.* 183, 2232-2241 (2009)). These effects are mediated via TLR signaling and via interactions with the HA receptor CD44.

In the healthy CNS, astrocytes are the main producers of low levels of HA, depositing it as ECM complexes in the spaces between myelinated axons and between myelin sheaths and astrocyte processes (Asher, R., et al., *J. Neurosci. Res.* 28, 410-421 (1991)). Upon injury, however, reactive astrocytes produce abundant amounts of HA, which accumulate in damaged areas (Back, S. A. et al., *Nat. Med.* 11, 966-972 (2005); Bugiani, M. et al., *Brain* 136, 209-222 (2013)). As such, HA is present at high levels in demyelinating lesions in MS patients and in mice with EAE (Back, S. A. et al., *Nat. Med.* 11, 966-972 (2005)).

Recently, it was shown that HA deposits accumulate within the pancreatic islets of individuals with recent-onset T1D (Bogdani, M. et al., *Diabetes* 63, 2727-2743 (2014)). These deposits were present at sites of insulitis (Bogdani, M. et al., *Diabetes* 63, 2727-2743 (2014)). Similar HA deposits were observed in animal models of T1D (Nagy, N. et al., *J. Clin. Invest.* 125, 10.1172/JCI79271-0 (2015)).

Many other chronic inflammatory diseases are also associated with HA deposition. For example, the pathogenesis of T2D is known to have an inflammatory component with inflammation localized to the muscle and adipose tissue (Wellen, K. E. and Hotamisligil, G. S., *J. Clin. Invest.* 115, 1111-1119 (2005)). In T2D HA deposition has been noted in skeletal muscle (Kang, L. et al., *Diabetes* 62, 1888-1896 (2013)), adipose tissue (Liu, L. F. et al., *Diabetologia* 58, 1579-1586 (2015)), and other tissues of obese and diabetic animals (Mine, S., et al., *Endocr.* 1 53, 761-766 (2006); Bowling, F. L., et al., *Nat Rev Endocrinol.* 11, 606-616 (2015); Dalferes, E. R., et al., *Proc. Soc. Exp. Biol. Med.* 148, 918-924 (1975); Dwyer, T. M. et al., *Kidney Int.* 58, 721-729 (2000); Zhu, Y., et al., *Sci. Transl. Med* 8, 323ps4-323ps4 (2016)). As another example many cancers are also associated with abundant HA in the matrix surrounding tumors (Li, Y. and Heldin, P., *Br. J. Cancer* 85, 600-607 (2001); Schwertfeger, K. L., et al., *Front. Immunol.* 6, 236 (2015)).

HA Synthesis Inhibitors

4-MU is a selective inhibitor of HA synthesis. The compound was first used in vitro in 1990 by Nakamura et al., to inhibit HA-synthesis in skin fibroblasts (Nakamura, T. et al., *Biochem. Biophys. Res. Commun.* 172, 70-76 (1990)). In 2004, the mechanism of 4-MU was discovered by Kakizaki et al., and since then it has been used in in vivo studies in mice and rats to investigate the 4-MU influence, mainly in cancer studies (Kakizaki, I. et al., *J. Biol. Chem.* 279, 33281-33289 (2004)); see also, e.g., Yoshihara, S. et al., *FEBS Lett.* 579, 2722-2726 (2005); Lokeshwar, V. B. et al., *Cancer Res.* 70, 2613-2623 (2010) and in atherosclerosis studies (Nagy, N. et al., *Circulation* 122, 2313-2322 (2010)). 4-MU is also already used in humans. It is available without a prescription as Heparvit, a nutraceutical product for cancer patients. Furthermore, it is available with prescription in Europe and Asia to treat biliary spasm under the name Hymecromone. In that setting, the drug has an excellent safety profile and has been used for several years.

One strategy to decrease or prevent the pro-inflammatory activity of LMW-HA within autoimmune lesions is to limit HA synthesis using 4-MU. 4-MU is a derivate that belongs to the coumarin family. Other coumarin derivatives, such as phenprocoumon (Marcumar®) and warfarin (Coumadin®), are used in preventive medicine to reduce cardiovascular events due to their anticoagulatory mechanism. 4-MU is thought to inhibit HA production in at least two ways. First, 4-MU is thought to function as a competitive substrate for UDP-glucuronyltransferase (UGT), an enzyme involved in HA synthesis (Kakiazaki, I., et al., *J. Biol. Chem.* 279, 33281-33289 (2004)). HA is produced by the HA synthases HAS1, HAS2 and HAS3 from the precursors UDP-glucuronic acid (UDP-GlcUA) and UDP-N-acetyl-glucosamine (UDP-GlcNAc). These are generated by the transfer of an UDP-residue to N-acetylglucosamine and glucuronic acid via the UDP-glucuryltransferase (UGT). The availability of UDP-GlcUA and UDP-GlcNAc thereby control HA synthesis (Vigetti, D. et al., *J. Biol. Chem.* 281, 8254-8263 (2006)). In the presence of 4-MU, it covalently binds through its hydroxyl group at position 4 to glucuronic acid via the UGT. As a consequence, the concentration of UDP-glucuronic acid declines in the cytosol and HA synthesis is reduced. This therewith reduces 4-MU the UDP-GlcUA content inside the cells. 4-MU inhibits HA synthesis by depleting the HAS enzyme UDP-GlcUA, which is consumed by 4-MU glucuronidation. So far it is unclear how exactly the second mechanism works, but, 4-MU reduces expression of HAS mRNA expression (Kultti A., et al., *Exp. Cell Res.* 315, 1914-1923 (2009) as well as mRNA for UDP glucose pyrophosphorylase and dehydrogenase (Vigetti, D. et al., *Glycobiology* 19, 537-546 (2009)).

A few studies have investigated the impact of 4-MU on HA synthesis in autoimmunity and inflammation. 4-MU has been used to inhibit HA production by several human pathogens and their interactions with human cells in vitro (Jong, A. et al., *Eukaryotic Cell* 6, 1486-1496 (2007); Kakizaki, I. et al., *Eur. J. Biochem.* 269, 5066-5075 (2002)). In vivo studies showed that 4-MU treatment decreased or prevented lung injury and reduced inflammatory cytokine levels in mouse models of staphylococcal enterotoxin-mediated (McKallip, R. J., et al., *Toxins (Basel)* 5, 1814-1826 (2013)) and lipopolysaccharide-mediated acute lung injury (McKallip, R. J., et al., *Inflammation* 38, 1250-1259 (2015)). 4-MU has also been shown to have protective effects on non-infectious inflammation, including renal ischemia and reperfusion (Colombaro, V. et al., *Nephrol. Dial. Transplant.* 28, 2484-2493 (2013)), and airway inflammation secondary to cigarette smoke, 4-MU also restores normoglycemia and promotes insulin sensitivity in obese, diabetic mice via increased production of adiponectin (Sim, M.-O., et al., *Chem. Biol. Interact.* 216, 9-16 (2014)). 4-MU has also been reported to ameliorate disease in a limited number of mouse models of autoimmune disease. Specifically, 4-MU treatment was beneficial in the collagen-induced arthritis model where it improved disease scores and reduced expression of matrix metaloproteases (MMPs) (Yoshioka Y, et al., *Arthritis Rheum.* 65, 1160-1170 (2013)). More recently, 4-MU treatment was demonstrated to prevent and treat disease in the experimental autoimmune encephalomyelitis (EAE) model where it increased populations of regulatory T-cells and polarized T-cell differentiation away from pathogenic, T-helper 1 T-cell subsets and towards non-pathogenic T-helper 2 subsets (Mueller, A. M., et al., *J. Biol. Chem.* 289, 22888-22899 (2014)). In addition, 4-MU treatment reduced the number of tumor satellites, inhibited angiogenesis and cell growth in tumors (Yoshihara, S. et al., *FEBS Lett.* 579, 2722-2726 (2005); Lokeshwar, V. B. et al., *Cancer Res.* 70, 2613-2623 (2010); Garcia-Vilas, J. A., et al., *J. Agric. Food Chem.* 61, 4063-4071 (2013)). The existing in vitro and in vivo data suggest that hymecromone can have utility as a component of therapeutic regimens directed against HA-producing cancers.

4-MU treatment has been reported to reduce or prevent cell-cell interactions required for antigen presentation (Bollyky, P. L. et al., *Cell. Mol. Immunol.* 7, 211-220 (2010)) and has been described to have inhibitory effects on T-cell proliferation (Mahaffey, C. L. and Mummert, M. E., *J. Immunol.* 179, 8191-8199 (2007); Mummert, M. E. et al., *J. Immunol.* 169, 4322-4331 (2002)). These effects are consistent with established roles for HA and its receptors in T-cell proliferation, activation, and differentiation (Jiang, D., Liang, J. and Noble, P. W., *Physiol. Rev.* 91, 221-264 (2011); Guan, H., et al., *J. Immunol.* 183, 172-180 (2009); Ponta, H., et al., *Nat. Rev. Mol. Cell Biol.* 4, 33-45 (2003)). There are also indications that 4-MU treatment can make some models of inflammation worse. 4-MU treatment was associated with worse atherosclerosis in ApoE-deficient mice fed a high-fat diet (Nagy, N. et al., *Circulation* 122, 2313-2322 (2010)).

4-MU treatment has been reported to limit the progression of EAE (Mueller, A. M., et al., *J. Biol. Chem.* 289, 22888-22899 (2014); Kuipers, H. F. et al., *Proc. Natl. Acad. Sci. U.S.A.* 113, 1339-1344 (2016)) and autoimmune diabetes in both the DORmO and NOD mouse models (Nagy, N. et al., *J. Clin. Invest.* 125, 10.1172/JCI79271-0 (2015); Kuipers, H. F. et al., *Clin. Exp. Immunol.* 185, 372-381 (2016)). This therapeutic effect was not only a result of the polarization of the T-cell response away from a pathogenic Th1 response, but also the reduction of infiltration of these cells into sites of autoimmune attack. Additionally, because 4-MU treatment lifts the inhibition of FoxP3+ Treg induction and function by LMW-HA, this inhibition of the pathogenic response is aided by an increase of Treg numbers (Nagy, N. et al., *J. Clin. Invest.* 125, 10.1172/JCI79271-0 (2015); Kuipers, H. F. et al., *Proc. Natl. Acad. Sci. U.S.A.* 113, 1339-1344 (2016); Kuipers, H. F. et al., *Clin. Exp. Immunol.* 185, 372-381 (2016)). Furthermore, in addition to sustaining a pro-inflammatory environment in MS lesions, HA deposits have been show to inhibit the maturation of oligodendrocytes, the myelin forming cells of the CNS, in MS and other myelin degenerative disorders, and as such are thought to prevent repair of myelin, further contributing to MS pathogenesis (Back, S. A. et al., *Nat. Med.* 11, 966-972 (2005); Bugiani, M. et al., *Brain* 136, 209-222 (2013)). 4-MU treatment can restore the HA load in inflamed tissues to a dominance of anti-inflammatory high molecular weight (HMW) polymers.

4-MU treatment for immune modulation is discussed in U.S. Publication No. 2016/0184262, which is assigned to assignees for the present application and is incorporated herein by reference in its entirety.

Since more and more studies highlight the role of HA in inflammation, autoimmunity, and cancer, there has been great interest in identifying pharmacologic tools to inhibit HA synthesis. 4-MU has been shown to inhibit HA production in multiple cell lines and tissue types both in vitro and in vivo (Nagy, N. et al., *Circulation* 122, 2313-2322 (2010); Kakiazaki, I., et al., *J. Biol. Chem.* 279, 33281-33289 (2004); Kultti A., et al., *Exp. Cell Res.* 315, 1914-1923 (2009); Bollyky, P. L. et al., *Cell. Mol. Immunol.* 7, 211-220 (2010)), and has received much attention as a potential therapeutic in inflammation, autoimmunity and cancer (Nagy, N. et al., *Front Immunol.* 6, 123 (2015)), unrelated to its clinical use for bile duct disorders (Abate, A. et al., *Drugs Exp. Clin. Res.* 27, 223-231 (2001)). Unfortunately, 4-MU has poor pharmacokinetics and limited bioavailability outside the liver and biliary tract (Nagy, N. et al., *Front Immunol.* 6, 123 (2015); Garrett, E. R., et al., *Biopharm Drug Dispos* 14, 13-39 (1993); Garrett, E. R. and Venitz, J., *J. Pharm. Sci.* 83, 115-116 (1994)).

There is a need for HA synthesis inhibitors that can provide a safe and effective therapy for, for example, autoimmune diseases such as, for example, diabetes and MS and for inflammatory disorders, such as, for example, diabetes and cancer. Furthermore, although it is known that HA deposits are abundant in chronically inflamed tissues and that 4-MU is a selective inhibitor of HA synthesis, there remains a need to develop a safe and effective therapy for PSC. The present disclosure seeks to fulfill these needs and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a method of treating an autoimmune condition, such as primary sclerosing cholangitis (PSC) in a subject including selecting a subject afflicted with or at risk of developing PSC; and administering to the subject a therapeutically effective amount of 4-methylumbelliferone (4-MU) or a metabolite thereof, or a pharmaceutically acceptable salt, ester or prodrug thereof; wherein the progression of PSC is reduced. The reduction in the progression of PSC can be a qualitative improvement in the anatomy of the subject's biliary tree as assessed by magnetic resonance cholangiopancreatography. Biliary tract fibrosis can be reduced or the progression of biliary tract fibrosis may be reduced. The reduction of biliary tract fibrosis or a reduction of the progression of biliary tract fibrosis can be measured by an enhanced liver fibrosis score. The progression of PSC can be measured by a reduction in serum levels of alkaline phosphatase, aspartate aminotransferase, alanine transaminase (ALT), gamma-glutamyl transferase (GGT) or bilirubin. In some aspects of the method, a hyaluronan (HA) level is reduced. The reduction of HA can be measured by a reduction in serum levels of HA. Further, in some aspects of the method, serum levels of alkaline phosphatase aspartate aminotransferase, alanine transaminase (ALT), gamma-glutamyl transferase (GGT) or bilirubin in the subject can be reduced. In addition choleresis can be improved, and/or regulatory T cells (Tregs) can be induced. In some aspects of the method, the administering can be intravenous or subcutaneous.

Other features and advantages will be apparent from the following detailed description, the drawings, and the claims.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 illustrates the chemical structure of 4-methylunbelliferone (4-MU), 4-methylumbelliferyl sulphate (4-MUS), and 4-methylumbelliferyl glucuronide (4-MUG), and graphically represents a concentration of 4-MU and its metabolites 4-MUG and 4-MUS following administration of 4-MU.

FIG. 2 illustrates the structure and formulae of embodiments of 4-MUG derivatives of the present disclosure.

FIG. 3 illustrates the structure of 4-MU and graphically represents a concentration of HA following exposure to 4-MU.

FIG. 4 illustrates the structure of 4-MUG and graphically represents a concentration of HA following exposure to 4-MUG.

FIG. 5 shows the structure of ethyl-4-MUG and graphically represents a concentration of HA following exposure to ethyl-4-MUG.

FIG. 6 shows the structure of ethyl-4-MUG-Ac and graphically represents a concentration of HA following exposure to ethyl-4-MUG-Ac.

FIG. 7 shows the structure of butyl-4-MUG and graphically represents a concentration of HA following exposure to butyl-4-MUG-Ac.

FIG. 8 shows the structure of butyl-4-MUG-Ac and graphically represents a concentration of HA following exposure to butyl-4-MUG-Ac.

FIG. 11A graphically represent the induction of FoxP3+ regulatory T-cells by 4-MUG. 4-MUG does not increase the numbers of CD3+ T-cells FIG. 11B graphically represent the induction of FoxP3+ regulatory T-cells by 4-MUG. 4-MUG does not increase the numbers of CD4+ T-cells.

FIG. 11C graphically represent the induction of FoxP3+ regulatory T-cells by 4-MUG. 4-MUG does not increase the numbers of CD25+ T-cells.

FIG. 11D graphically represent the induction of FoxP3+ regulatory T-cells by 4-MUG. 4-MUG increases the fraction of Foxp3+ regulatory T-cells. This indicates a specific effect on Foxp3+T regulatory T-cells.

FIG. 14A illustrates the proximal and distal ends of a major papilla showing a stricture of intrahepatic duct, a stricture of common hepatic duct, a fibrotic stricture showing dilated lumen and inflammation (thickening) of wall.

FIG. 14B shows a dilated lumen of intrahepatic ducts, a stricture and cholecystectomy clips.

DETAILED DESCRIPTION

Figure 9:
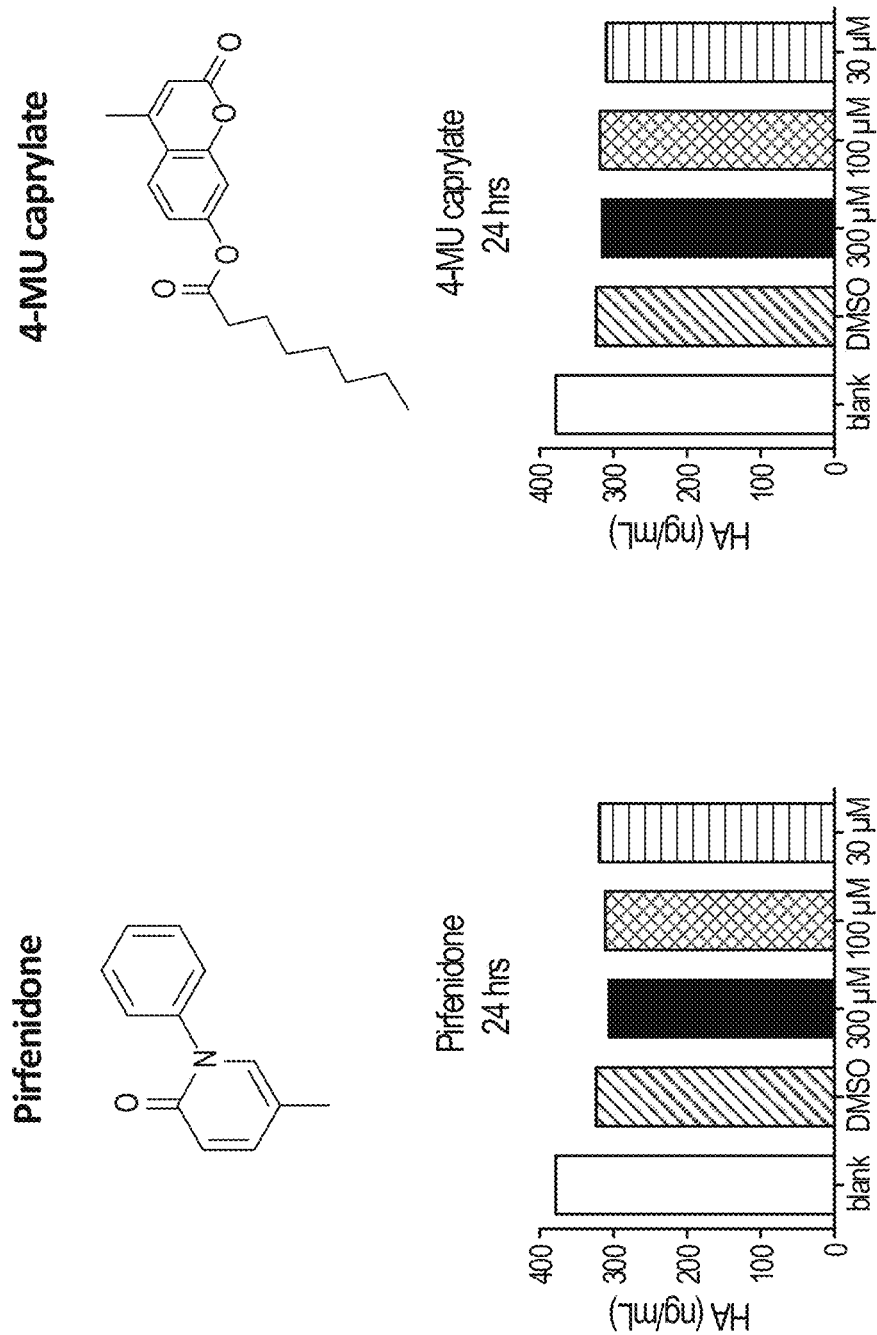
FIG. 9 shows the structure of pirfenidone and 4-MU caprilate and graphically represents a concentration of HA following exposure to pirfenidone and 4-MU caprilate.

Hyaluronan (HA) is an inflammatory mediator that is abundant at sites of chronic diseases of diverse etiologies, including autoimmunity, infection, and cancer. It would be useful to be able to inhibit HA synthesis pharmacologically. One drug that does this is 4-methylumbelliferone. 4-methylumbelliferone glucuronide (4-MUG), a metabolite of 4-MU, is biologically active and inhibits HA synthesis. Previously it was not known that 4-MUG is an inhibitor of HA synthesis. Indeed, the established understanding of the mechanism of action of 4-MU would suggest that it should not be. However, the present disclosure (and the Examples below) show that 4-MUG surprisingly inhibits HA synthesis as effectively as 4-MU. This disclosure presents 4-MUG derivatives (e.g., 4-MUG ester prodrugs) that reduce or prevent HA synthesis. The 4-MUG derivatives of the present disclosure can be used to suppress HA synthesis and curtail inflammation.

Primary Sclerosing Cholangitis Treatment

"Cholangitis" often means bacterial cholangitis, and acute cholangitis is bacterial in nature. In some aspects, bacterial cholangitis, either acute or chronic, and cholangitis caused by infection, are excluded from the treatment herein. See Garrett et al., *Biopharmaceuticals & Drug Disposition* 14.1 (1993):13-39 and Kakiuchi et al., *Nippon Shokakibyo Gakkai Zasshi* 72:3, 260-70 (1975). In some aspects, secondary causes of sclerosing cholangitis, such as surgical trauma, presence of intraductal stones or recurrent episodes of inflammation are likewise excluded from the treatment herein.

Without wishing to be bound by theory, it is believed that the 4-MU, 4-MUG, and 4-MUG derivatives of the present disclosure overcome many of the disadvantages of prior attempted PSC treatments. It is believed that the 4-MU, 4-MUG, and 4-MUG derivatives of the present disclosure attack the quintessential triad of this disease: autoimmune attack, cholestasis, and inflammation leading to fibrosis.

First, regarding autoimmune attack on the biliary duct epithelium, multiple animal studies show that 4-MU has an immuno-modulatory effect in autoimmune diseases by inducing regulatory T cells (Tregs). 4-MU has been shown to be an inducer of Treg. Its Treg induction causes a disease-modifying impact in several animal models of autoimmunity, namely Type 1 Diabetes, multiple sclerosis, and rheumatoid arthritis. As Treg induction has been shown to have far-reaching and expansive impact on a spectrum of autoimmune diseases, the PSC disease state is expected to be ameliorated by an increased count of Treg caused by 4-MU.

Second, regarding the further weakening of the integrity of the biliary duct by cholestasis, 4-MU has been used for over 50 years across Europe and Asia as a treatment for biliary dyskinesia. Several published clinical trials support 4-MU's choleretic and anti-spasmodic effects, for example, as described in Abate, et al., *Drugs Exp. Clin. Res.* 27(5-6): 223-31 (2001).

Furthermore, it is believed that 4-MU is a true choleretic that shows spasmolytic activity on the gall bladder and more especially on the sphincter of Oddi, while it lacks spasmolytic effects on other organs. 4-MU re-stabilizes biliary function in its integrity thanks to its doubly beneficial mode of action. For example, 4-MU can provide elective antispastic action on the gall bladder and the sphincter of Oddi; and gentle and protracted choleretic action without any cholagogic effects.

Many of the symptoms of PSC and a significant cause of the progression of the disease is the back-up of hydrophobic bile acids. These stagnant pools of bile acids act like a detergent against the cell membranes of the bile ducts causing cumulative damage. Simply getting the bile flow moving is likely to have a dramatic impact on hepatotoxicity of the bile acids. This effect may be shown via a reduction in biochemical markers of hepatic distress. Reduction of serum ALP is commonly used as a surrogate for clinical benefit in liver diseases.

Third, regarding chronic inflammation which leads to progressive liver fibrosis, HA is known to be a mediator of the inflammatory response, and 4-MU reduces HA. In inflammatory settings, lowering local HA synthesis lowers local levels of inflammation. Lower levels of inflammation reduce the production of fibrotic scar tissue. An accumulation of HA is so integral to the progression of fibrosis that it is used as a prognostic indicator of the disease and is a major component of the aforementioned enhanced liver fibrosis (ELF) score. As 4-MU is a strong inhibitor of hyaluronan synthesis, it is believed to have an impact on the chronic inflammation pervasive in the bile ducts of patients with PSC. Without wishing to be by theory, it is believed that 4-MU has been shown to reduce fibrosis in an animal model of cholestasis (the Biliary Duct Ligation (BDL) model) (Sawada, *Hirosaki Med.* 1, 66: 143-151, 2016). However, as this model has no autoimmune component and the bile flow is completely blocked, it is believed that the beneficial effects are due to reduction of HA synthesis and a concomitant reduction in inflammation and fibrosis.

In addition to having the above properties, it is believed that 4-MU has the added benefit of being concentrated in the hepatic and biliary system pending excretion. In fact, extraction by the liver is as high as 97%. Because of this, doses of 4-MU, 4-MUG, and 4-MUG derivatives that would have modest systemic effect can be administered at therapeutically effective dose in patients with PSC. This can provide specificity to the treatment lacking for other immunomodulators, and gives greater confidence in the drug's toxicity profile. It is believed that conventional therapies for PSC are inadequate or have unwanted side effects and therefore the present compound and compositions are useful in treating these diseases.

U.S. Pat. No. 10,285,976, which is incorporated herein by reference in its entirety, relates to compositions for treating autoimmune, allergic, or atopic disease including a compound that inhibits hyaluronan synthesis and a pharmaceutically acceptable carrier. A compound that inhibits hyaluronan synthesis is 4-methylumbelliferone or a metabolite of 4-methylumbelliferone. Methods for treating autoimmune diabetes, multiple sclerosis and/or autoimmune demyelination, including administering to the subject a composition having a compound in an amount effective to inhibit hyaluronan synthesis in a mammalian subject, are also described in this application.

In treating PSC, ELF scores may improve, as discussed above, and/or choleresis may improve. Cholerisis may be measured by cannulation of the bile duct. For example, cannulation may include surgically implanting a tube into the bile duct, and collecting samples.

In some embodiments, compounds disclosed in U.S. Pat. No. 10,285,976 and the present application are suitable for treating PSC as described herein. For instance, compounds for treating PSC can include a compound that inhibits hyaluronan synthesis in a subject, a compound that induces a regulatory T-cell response in a subject, and/or a compound that increases FoxP3+ regulatory T-cells in a subject. In some instances, a compound suitable for treating PSC is a compound that binds glucuronic acid. In some instances, a compound suitable for treating PSC is a UDP glycosyltransferase inhibitor or a UDP-glucuronyltransferase inhibitor.

The present disclosure features a method of treating primary sclerosing cholangitis (PSC) in a subject including selecting a subject afflicted with or at risk of developing PSC; and administering to the subject a therapeutically effective amount of 4-methylumbelliferone (4-MU), a metabolite thereof, a metabolite derivative thereof, an ester thereof, prodrug thereof, or a pharmaceutically acceptable salt thereof; wherein the progression of PSC is reduced (e.g., following administration of a therapeutically effective amount of 4-methylumbelliferone (4-MU), a metabolite thereof, a metabolite derivative thereof, an ester thereof, prodrug thereof, or a pharmaceutically acceptable salt thereof).

In some embodiments, PSC disease progression indicators can be used to monitor the effectiveness of the treatment methods of the present disclosure. As discussed above, in PSC, a patient's own immune system systematically attacks the epithelium of the bile duct system. Constant injury to the epithelium can lead to biliary dysfunction. As the epithelial cells of the biliary tract begin to die from the chronic inflammatory response, fibrosis ensues, strictures begin to form, which physically obstruct the flow of bile (cholestasis). Thus, amelioration of the underlying autoimmune attack and the concomitant cholestasis can be used to monitor the effectiveness of the treatment methods.

As discussed above, as the epithelial cells succumb to this knock-out blow, a biochemical response can be detected: a rise in hepatic enzymes and bilirubin in the blood stream, which are markers for hepatic damage. The first signals are a rise in serum transaminase levels: AST (aspartate aminotransferase) and ALT (alanine aminotransferase) and ALP (alkaline phosphatase). This is followed by a rise in bilirubin. A reduction of hepatic damage or a reduction of the progression of hepatic damage is measured by a reduction in serum levels of ALP, AST, ALT, gamma-glutamyl transferase (GGT), and/or bilirubin. Clinical signs associated with cholestasis can also be used to monitor the effectiveness of the treatment methods: namely an improvement in fatigue, jaundice, and/or pruritus (caused by bile acid build up in the skin). In some embodiments, portal hypertension and/or fibrosis can be used to monitor the treatment method effectiveness.

In some embodiments, prognostic indicators of PSC disease progression can be used to monitor PSC and the effectiveness of the treatment. The most commonly used, validated prognostic models for the progression of PSC are the revised Mayo Model and the Enhanced Liver Fibrosis Score.

The Revised Mayo Model is a multi-variate analysis of survival studies in PSC, wherein five independent markers were identified: 1) Age; 2) Serum Bilirubin; 3) Serum Albumin; 4) Serum AST Levels; and 5) Presence of variceal hemorrhage. The Mayo Clinic formulated a composite score of these markers which is now called the Revised Mayo Model. A website that calculates a patient's Mayo score and provides the patient's estimated probability of survival over the next 4 years is found at www.mayoclinic.org/medical-professionals/model-end-stage-liver-disease/revised-natural-history-model-for-primary-sclerosing-chonalgitis. The Revised Mayo Model is a widely accepted, useful tool for assessing the prognosis of a patient with PSC and for determining the appropriate timing of liver transplantation.

The Enhanced Liver Fibrosis (ELF) score is also a validated, prognostic tool of transplant-free survival in PSC, independent of the Mayo score. It is an algorithm that directly measures the level of liver fibrosis by analyzing: 1) Serum Levels of Hyaluronic Acid (primary cleared through hepatic sinusoids); 2) Tissue Inhibitor of Metalloproteinases-1 (TIMP1) (TIMP1 plays a crucial role in extracellular matrix (ECM) composition); and 3) Pro-peptide of Type III Procollagen (reflects new collagen synthesis). A higher concentration of individual biomarkers leads to a higher ELF score and indicates a greater likelihood of more severe fibrosis and thus lower survival. A reduction of one or more individual biomarkers may indicate that fibrosis is reduced or the progression of fibrosis is reduced, and leads to a lower ELF score. An ELF blood test may be used to determine the levels of various biomarkers. In some aspects, a reduction in ELF score indicates a reduction of fibrosis. A reduction of fibrosis or a reduction of the progression of fibrosis may be measured by an ELF score that is the same as or lower than the ELF score before treatment. Xie, et al, *PLOS ONE,* 9:4 e92772 (2014).

Figure 16:
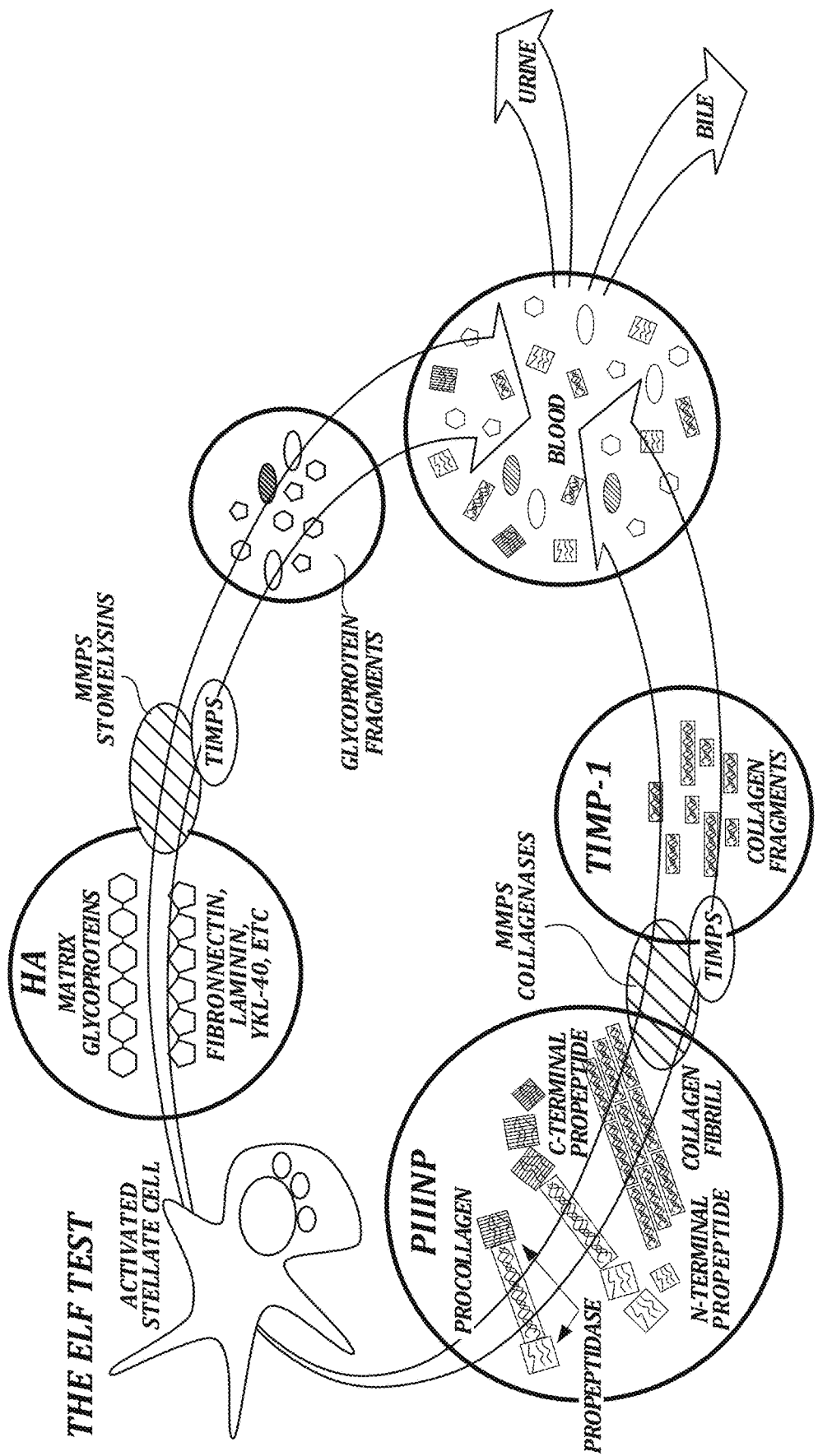
FIG. 16 illustrates Enhanced Liver Fibrosis (ELF) score biomarkers according to the ELF test.

The ELF test (FIG. 16) was clinically validated in an international multicenter study with a mix of patient groups and was found to be accurate to differentiate mild, moderate, and severe fibrosis. The ELF test subsequently has been shown to be at least as accurate as biopsy at predicting liver disease-related outcomes.

In addition, HA levels reflect PSC progression as well as serial biopsy or elastography.

In some embodiments, the reduction in the progression of PSC is a qualitative improvement in the anatomy of the subject's biliary tree as assessed by magnetic resonance cholangiopancreatography.

In some embodiments, in the treatment of PSC, the biliary tract fibrosis is reduced or the progression of biliary tract fibrosis is reduced following administration of a therapeutically effective amount of 4-methylumbelliferone (4-MU), a metabolite thereof, a metabolite derivative thereof, an ester thereof, prodrug thereof, or a pharmaceutically acceptable salt thereof. In some embodiments, in the treatment of PSC, the biliary tract fibrosis is reduced or the progression of biliary tract fibrosis is reduced following administration of a therapeutically effective amount of 4-methylumbelliferone (4-MU), a metabolite thereof, an ester thereof, prodrug thereof, or a pharmaceutically acceptable salt thereof. The reduction of biliary tract fibrosis or a reduction of the progression of biliary tract fibrosis can be measured by an enhanced liver fibrosis score. The reduction of the progression of PSC can be measured by a reduction in serum levels of alkaline phosphatase, aspartate aminotransferase, alanine transaminase (ALT), gamma-glutamyl transferase (GGT), and/or bilirubin.

In some embodiments, in the treatment of PSC, a hyaluronan (HA) level is reduced following administration of a therapeutically effective amount of 4-methylumbelliferone (4-MU), a metabolite thereof, a metabolite derivative thereof, an ester thereof, prodrug thereof, or a pharmaceutically acceptable salt thereof. In some embodiments, the reduction of HA is measured by a reduction in serum levels of HA.

In some embodiments, in the treatment of PSC, the serum levels of alkaline phosphatase aspartate aminotransferase, alanine transaminase (ALT), gamma-glutamyl transferase (GGT), and/or bilirubin in the subject are reduced following administration of a therapeutically effective amount of 4-methylumbelliferone (4-MU), a metabolite thereof, a metabolite derivative thereof, an ester thereof, prodrug thereof, or a pharmaceutically acceptable salt thereof.

In some embodiments, in the treatment of PSC, choleresis is improved following administration of a therapeutically effective amount of 4-methylumbelliferone (4-MU), a metabolite thereof, a metabolite derivative thereof, an ester thereof, prodrug thereof, or a pharmaceutically acceptable salt thereof.

In some embodiments, in the treatment of PSC, regulatory T cells (Tregs) are induced following administration of a therapeutically effective amount of 4-methylumbelliferone (4-MU), a metabolite thereof, a metabolite derivative thereof, an ester thereof, prodrug thereof, or a pharmaceutically acceptable salt thereof.

In some embodiments, the therapeutically effective amount of 4-methylumbelliferone (4-MU), a metabolite thereof, a metabolite derivative thereof, an ester thereof, prodrug thereof, or a pharmaceutically acceptable salt thereof is administered intravenously or subcutaneously.

In some embodiments, treating PSC includes administering a therapeutically effective amount of 4-methylumbelliferone (4-MU) or a pharmaceutically acceptable salt thereof. In some embodiments, treating PSC includes administering a therapeutically effective amount of a metabolite of 4-MU, such as 4-MUG, or a pharmaceutically acceptable salt thereof. In some embodiments, treating PSC includes administering a therapeutically effective amount of a derivative of 4-MUG or a pharmaceutically acceptable salt thereof. In some embodiments, treating PSC includes administering a therapeutically effective amount of an ester of 4-MU or a pharmaceutically acceptable salt thereof. In some embodiments, treating PSC includes administering a therapeutically effective amount of 4-methylumbelliferone (4-MU), a metabolite thereof, a metabolite derivative thereof, an ester thereof, or a pharmaceutically acceptable salt thereof. In some embodiments, treating PSC includes administering a therapeutically effective amount of 4-methylumbelliferone (4-MU), a metabolite thereof, an ester thereof, or a pharmaceutically acceptable salt thereof. In some embodiments, treating PSC includes administering a therapeutically effective amount of 4-methylumbelliferone (4-MU), an ester thereof, or a pharmaceutically acceptable salt thereof.

4-Methylumbelliferone metabolite derivatives are described in greater detail below.

Definitions

Unless specifically defined herein, all terms used herein have the same meaning as they would to one skilled in the art of the present disclosure. The following definitions are provided in order to provide clarity with respect to the terms as they are used in the specification and claims to describe the claimed subject matter.

As used herein, the term "regulatory T-cells" or "Treg" cells refers to T-cells which express the cell surface markers CD4+ and CD25+, which express FoxP3 protein as measured by a Western blot and/or FoxP3 mRNA transcript.

As used herein, the term "antigen-specific regulatory T-cells" or "antigen-specific Tregs" refers to Treg cells that were induced in the presence of an antigen and which express the cell surface markers CD4+ and CD25+, which express FoxP3 protein as measured by a Western blot and/or FoxP3 mRNA transcript.

As used herein, the term "derived from" or "a derivative thereof," in the context of peptide or polypeptide sequences, means that the peptide or polypeptide is not limited to the specific sequence described, but also includes variations in that sequence, which can include amino acid additions, deletions, substitutions, or modifications to the extent that the variations in the listed sequence retain the ability to modulate an immune response. In the context of small molecules (i.e., an organic compound having a molecular weight of less than about 1000 Da that can help regulate biological process, with a size on the order of 1 nm), a derivative is a small molecule that has been modified by chemical reaction, such as by acylation, alkylation, halogenation, nitration, and/or cyanation.

As used herein, the term "peptide" or "polypeptide" is a linked sequence of amino acids and can be natural, recombinant, synthetic, or a modification or combination of natural, synthetic, and recombinant.

As used herein, the expression "effective amount" or "therapeutically effective amount" refers to an amount of the compound of the present disclosure that is effective to achieve a desired therapeutic result, such as, for example, the amelioration of PSC or improvement of a prognostic indicator of PSC disease progression. The compound of the present disclosure can be administered as a pharmaceutical composition comprising a therapeutically effective amount of the compound together with a pharmaceutically acceptable carrier. In the context of the present disclosure, a "therapeutically effective amount" is understood as the amount of a compound inhibiting the synthesis, expression, and/or activity of an identified HA polymer that is necessary to achieve the desired effect which, in this specific case, is treating PSC. Generally, the therapeutically effective amount of the compound according to the present disclosure to be administered will depend, among other factors, on the individual to be treated, on the severity of the disease the individual suffers, on the chosen dosage form, and the like. For this reason, the doses mentioned in the present disclosure must be considered only as a guideline for a person skilled in the art, and the skilled person must adjust the doses according to the previously mentioned variables. Nonetheless, a compound according to the present disclosure can be administered one or more times a day, for example, 1, 2, 3 or 4 times a day, in a typical total daily amount comprised between 0.1 µg to 10,000 mg/day, for example, 100 to 1,500 mg/day, 100 to 3,000 mg/day, or 900-2,700 mg/day such as, 900, 1,800 or 2,700 mg/day.

The subject can be a human or non-human animal, a vertebrate, and is typically an animal, including but not limited to, cows, pigs, horses, chickens, cats, dogs, and the like. More typically, the subject is a mammal, and in a particular embodiment, human.

As used herein, an "autoimmune disease" is a disease or disorder arising from and directed against an individual's own tissues. The absence or depletion of Treg can lead to autoimmune disease. Examples of autoimmune diseases or disorders include, but are not limited to, multiple sclerosis, arthritis (rheumatoid arthritis, juvenile rheumatoid arthritis, psoriatic arthritis), conditions involving infiltration of T-cells and chronic inflammatory responses, autoimmune myocarditis, pemphigus, T1D (also referred to as autoimmune diabetes or insulin-dependent diabetes mellitus, autoimmune lung disease, primary sclerosing cholangitis, autoimmune thyroid disease, autoimmune liver disease, lupus, rheumatoid arthritis, eczema, Sjögrens disease, lichen planus, and the like.

As used herein the term "treating" or "treatment" means the administration of a compound according to the disclosure to effectively prevent, repress, ameliorate, or eliminate at least one symptom associated with inflammatory, autoimmune, allergic, or atopic disease, including, for example, T1D, T2D, MS, Sjögrens disease, autoimmune thyroiditis, primary sclerosing cholangitis, rheumatoid arthritis, psoriasis, colitis, lichen planus, psoriasis, eczema, and asthma. Preventing at least one symptom involves administering a treatment to a subject prior to onset of the symptoms associated with clinical disease. Repressing at least one symptom involves administering a treatment to a subject after clinical appearance of the disease.

As noted above, HA is a polymer of disaccharides composed of glucuronic acid and N-acetylglucosamine and linked via alternating β-1,4 and β-1,3 glycosidic bonds. 4-MU functions as a competitive substrate for UGT, an enzyme involved in the synthesis of HA as well as bile (Kakizaki, I., et al., *J. Biol. Chem.* 279, 33281-33289 (2004)). 4-MU is used throughout Europe and Asia to prevent gallstones. It has been used for more than 30 years in both children and adults and has an excellent safety profile. It is available without prescription in the USA as a dietary supplement primarily marketed for use in people suffering from jaundice.

4-MU targets HA synthesis. Further, 4-MU can be used to abrogate PSC. Because 4-MU has no known toxicity, it has great potential in treating and preventing PSC.

Metabolites of 4-MU are also contemplated for the uses herein. Metabolites of 4-MU are described in, for example, Kakizaki, I., et al., *J. Biol. Chem.* 279, 33281-33289 (2004), and in Garrett, E. R., et al., *Biopharm. Drug Dispos.* 14, 13-39 (1994), both of which are incorporated herein by reference. Exemplary metabolites of 4-MU include 4-MUG and 4-MUS.

As used herein, the term "a subject suffering from autoimmune diabetes" refers to a subject suffering from an autoimmune disease that results in a high blood glucose level which can lead to serious problems with the heart, eyes, kidneys, nerves, and gums and teeth. Symptoms of autoimmune diabetes include, for example, being very thirsty, urinating often, feeling very hungry or tired, losing weight without trying, having sores that heal slowly, having dry, itchy skin, losing the feeling in the feet or having tingling in the feet, and/or having blurry eyesight.

As used herein, the term "a subject suffering from multiple sclerosis" refers to a subject suffering from an autoimmune disease that results in damage to the insulating covers of nerve cells in the brain and spinal cord or demyelination. Symptoms of MS include numbness or weakness in one or more limbs, partial or complete loss of central vision, usually in one eye, often with pain during eye movement (optic neuritis), double vision or blurring of vision, tingling or pain in parts of the body, electric-shock sensations that occur with certain head movements, tremor, lack of coordination or unsteady gait, slurred speech, fatigue, dizziness, and/or heat sensitivity, among others.

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the disclosure are stable. As used herein "stable" refers to a compound that is sufficiently robust to survive isolation to a useful degree of purity from a reaction mixture.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

"Optionally substituted" groups can refer to, for example, functional groups that can be substituted or unsubstituted by additional functional groups. For example, when a group is unsubstituted, it can be referred to as the group name, for example alkyl or aryl. When a group is substituted with additional functional groups, it can more generically be referred to as substituted alkyl or substituted aryl.

As used herein, the term "alkyl" is meant to refer to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 30, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "alkylene" refers to a linking alkyl group.

As used herein, "alkenyl" refers to an alkyl group having one or more double carbon-carbon bonds. The alkenyl group can be linear or branched. Example alkenyl groups include ethenyl, propenyl, and the like. An alkenyl group can contain from 2 to about 30, from 2 to about 24, from 2 to about 20, from 2 to about 10, from 2 to about 8, from 2 to about 6, or from 2 to about 4 carbon atoms.

As used herein, "alkenylene" refers to a linking alkenyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "haloalkylene" refers to a linking haloalkyl group.

As used herein, "haloalkenyl" refers to an alkenyl group having one or more halogen substituents.

As used herein, "haloalkenylene" refers to a linking haloalkenyl group.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "arylene" refers to a linking aryl group.

As used herein, a "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heteroarylene" refers to a linking heteroaryl group.

As used herein, "acyl" refers to any group or organic radical such as H, alkyl, or alkenyl (the alkyl or alkenyl can be further substituted with an alkyl, alkoxy, cycloalkylamino, hydroxy, or halo) attached to a carbonyl (C=O) moiety. The acyl group is attached to the parent structure through the carbonyl moiety.

As used herein, "heteroalkyl" refers to an alkyl group having at least one heteroatom such as sulfur, oxygen, or nitrogen.

As used herein, "heteroalkylene" refers to a linking heteroalkyl group.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-(haloalkyl) group.

As used herein, "cyano" refers to a —CN group.

As used herein, "nitro" refers to a —NO$_2$ group.

The compounds described herein can be asymmetric (e.g., having one or more stereocenters). All stereoisomers, such as enantiomers and diastereomers, are intended unless otherwise indicated.

Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and can be isolated as a mixture of isomers or as separated isomeric forms.

Compounds of the disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge.

Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the disclosure can also include all isotopes of atoms occurring in the intermediates or final compounds. Isotopes include those atoms having the same atomic number but different mass numbers. For example, isotopes of hydrogen include tritium and deuterium.

In some embodiments, the compounds of the disclosure, and salts thereof, are substantially isolated. By "substantially isolated" is meant that the compound is at least partially or substantially separated from the environment in which it was formed or detected. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

As used herein, the term "pharmaceutical composition" refers to a mixture of a compound disclosed herein with one or more other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

As used herein, the term "carrier" refers to a chemical compound that facilitates the incorporation of a compound into cells or tissues.

As used herein, the term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

As used herein, the term "physiologically acceptable" refers to a carrier or diluent that does not abrogate the biological activity and properties of the compound.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Derivatives, Dosage Forms and Pharmaceutical Compositions Useful for Methods Herein As discussed above, a metabolite, metabolite derivative, pharmaceutically-acceptable salt, ester, and/or prodrug of 4-MU can be used for the treatment methods of the present disclosure. Those skilled in the art will appreciate that a variety of prodrugs, salts, hydrates, solvates, and polymorphs can be produced from the compounds disclosed here, and that various isotopically-substituted variants (through, e.g., substitution of deuterium for hydrogen, C for carbon, N for nitrogen, or P for phosphorus) known as "isotopomers" can also be readily produced. All such derivatives are contemplated within the scope of this disclosure.

Many of the compounds may be in the form of a salt, but those skilled in medicinal chemistry will appreciate that the choice of salt is not critical, and other pharmaceutically-acceptable salts can be prepared by well-known methods. "Handbook of Pharmaceutical Salts: Properties, Selection and Use," (P. Heinrich Stahl and Camille G. Wermuth, eds.) *International Union of Pure and Applied Chemistry*, Wiley-VCH 2002 and L. D. Bighley, S. M. Berge, D. C. Monkhouse, in *Encyclopedia of Pharmaceutical Technology*, Eds. J. Swarbrick and J. C. Boylan, Vol. 13, Marcel Dekker, Inc., New York, Basel, Hong Kong 1995, pp. 453-499 discusses such salts in detail.

Compounds herein include those structures that are set out throughout the examples, and pharmaceutically acceptable salts, esters and prodrugs thereof. In some embodiments, the compound is in a pharmaceutical composition or a dosage form, wherein the pharmaceutical composition or dosage form provides an effective amount of the compound for treating or preventing the disease.

4-MUG Derivatives

The 4-methylumbelliferone glucuronide (4-MUG) derivatives of the present disclosure include a compound of Formula (I):

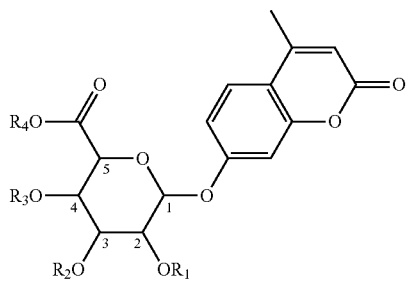
(I)

wherein $R_1$ and $R_2$ are each independently selected from H, C(O)—$C_{1-10}$ alkyl, and C(O)—$C_{1-10}$ haloalkyl;

$R_3$ is selected from H, C(O)—$C_{1-10}$ alkyl, C(O)—$C_{1-10}$ haloalkyl, C(O)—$C_{6-10}$ aryl, and C(O)—$C_{5-10}$ heteroaryl, wherein the C(O)—$C_{1-10}$ haloalkyl, C(O)—$C_{6-10}$ aryl, and C(O)—$C_{5-10}$ heteroaryl are each optionally substituted with 1, 2, 3, or 4 substituents independently selected from halo, cyano, and nitro; and $R_4$ is selected from $C_{2-10}$ alkyl and $C_{2-10}$ haloalkyl, or a pharmaceutically acceptable salt thereof.

The 1 to 5 carbon positions on the cyclic sugar moiety is indicated in Formula (I), above.

In some embodiments, $OR_1$ is in a down position at the 2-position in the cyclic sugar moiety:

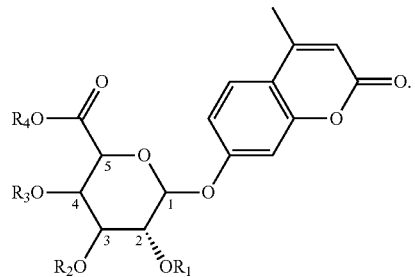

As used herein, the "up" or "down" position in a cyclic pyranose refers to the position of a substituent, for example, in a Haworth projection of the structures of the cyclic sugar, where the oxygen atom in the ring is drawn in the upper right-hand position of the hexagon, and the anomeric carbon refers to the 1-position in the cyclic sugar moiety. An up-position is oriented toward the top face of the ring, and the down position is oriented toward the bottom face of the ring.

In some embodiments, $OR_2$ is in an up position at the 3-position in the cyclic sugar moiety:

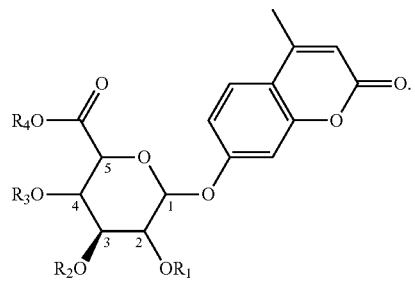

In some embodiments, $R_1$ and $R_2$ are each independently selected from H and C(O)—$C_{1-10}$ alkyl.

In some embodiments, $R_1$ and $R_2$ are each independently selected from H and C(O)—$C_{1-6}$ alkyl.

In some embodiments, $R_1$ and $R_2$ are each independently selected from H, C(O)-ethyl, and C(O)-methyl.

In some embodiments, $R_1$ and $R_2$ are each independently selected from H and C(O)-methyl.

In some embodiments, $OR_3$ is in a down position at the 4-position in the cyclic sugar moiety:

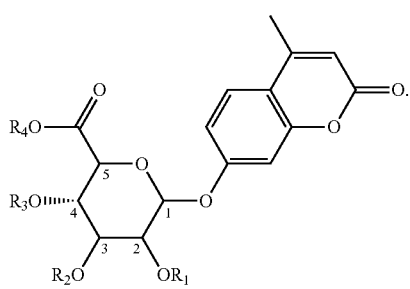

In some embodiments, $R_3$ is selected from H and C(O)—$C_{1-10}$ alkyl.

In some embodiments, $R_3$ is selected from H and C(O)—$C_{1-6}$ alkyl.

In some embodiments, $R_3$ is selected from H, C(O)-ethyl, and C(O)-methyl.

In some embodiments, $R_3$ is selected from H and C(O)-methyl.

In some embodiments, $C(O)OR_4$ is in an up position at the 5-position in the cyclic sugar moiety:

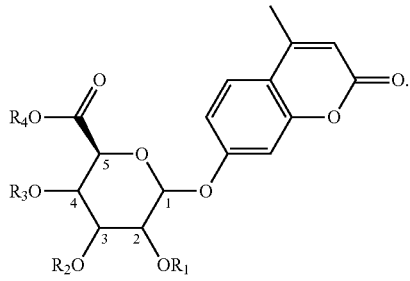

In some embodiments, $R_4$ is $C_{2-10}$ alkyl.

In some embodiments, $R_4$ is $C_{2-6}$ alkyl.

In some embodiments, $R_4$ is selected from ethyl, propyl, and butyl.

In some embodiments, $R_4$ is selected from ethyl and butyl.

In some embodiments, the 4-methylumbelliferone moiety is substituted in a β-anomeric position in the cyclic sugar moiety.

In some embodiments, the compound of Formula (I) is a 4-methylumbelliferone β-glucuronide:

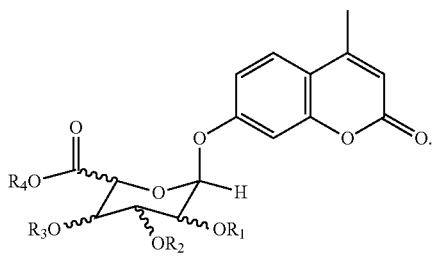

In some embodiments, the compound of claim 1 is selected from

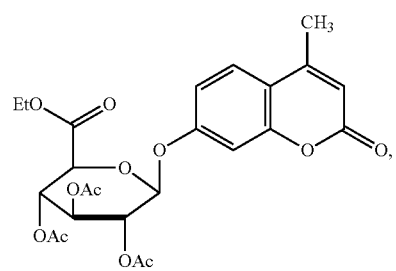

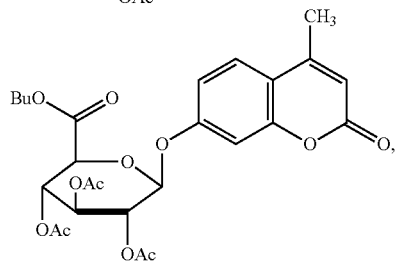

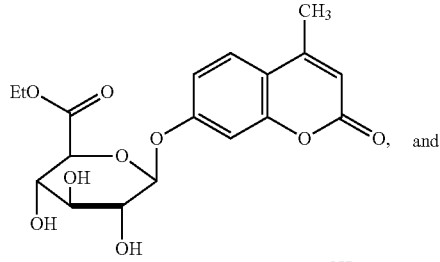

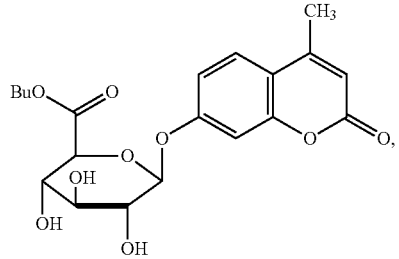

or a pharmaceutically acceptable salt thereof. As used herein, Bu refers to butyl, Et refers to ethyl, and Ac refers to acetyl.

In some embodiments, the present disclosure features a composition including a compound of Formula (I) as described above, or a pharmaceutically acceptable salt thereof, and a pharmaceutically acceptable carrier.

In some embodiments, the present disclosure features a method for intracellular delivery of a 4-methylumbelliferone-glucuronide derivative, including contacting a cell with a compound of Formula (I), or a pharmaceutically acceptable salt thereof, as described above.

In some embodiments, the present disclosure features a method of inducing a regulatory T-cell response, including administering to a subject a therapeutically effective amount of a compound of Formula (I), or a pharmaceutically acceptable salt thereof, as described above.

In some embodiments, the present disclosure features a method of inhibiting hyaluronan synthesis in a subject, including administering to the subject a therapeutically effective amount of a compound of Formula (I), or a pharmaceutically acceptable salt thereof, as described above.

In some embodiments, the present disclosure features a method of increasing FoxP3+ regulatory T-cells, including administering to a subject a therapeutically effective amount of a compound of Formula (I), or a pharmaceutically acceptable salt thereof, as described above.

In some embodiments, the present disclosure features a method of treating autoimmune, allergic, inflammatory, or atopic disease in a subject, including administering to the subject a therapeutically effective amount of a compound of Formula (I), or a pharmaceutically acceptable salt thereof, as described above. The autoimmune, allergic, or atopic disease can be selected from the group consisting of diabetes (type 1 and/or type 2), pre-diabetes, multiple sclerosis, Sjögrens disease, autoimmune thyroiditis, Lupus, rheumatoid arthritis, primary sclerosing cholangitis, psoriasis, colitis, eczema, and asthma.

In some embodiments, the present disclosure features a method for treating insulitis and/or reversing progression of autoimmune diabetes in a subject suffering from or at risk of developing autoimmune diabetes, the method including administering to the subject a composition including a compound of Formula (I), or a pharmaceutically acceptable salt thereof, in an amount effective to inhibit hyaluronan synthesis in the subject.

In some embodiments, the present disclosure features a method for treating multiple sclerosis in a subject in need thereof, the method including administering to the subject a composition including a compound of Formula (I), or a pharmaceutically acceptable salt thereof, in an amount effective to inhibit hyaluronan synthesis in the subject.

In some embodiments, the present disclosure features a method for treating multiple sclerosis and/or autoimmune demyelination in a subject suffering from or at risk of developing multiple sclerosis, the method including administering to the subject a composition comprising a compound of Formula (I), or a pharmaceutically acceptable salt thereof, in an amount effective to inhibit hyaluronan synthesis in the subject.

In some embodiments, the subject is a human.

Figure 10A:
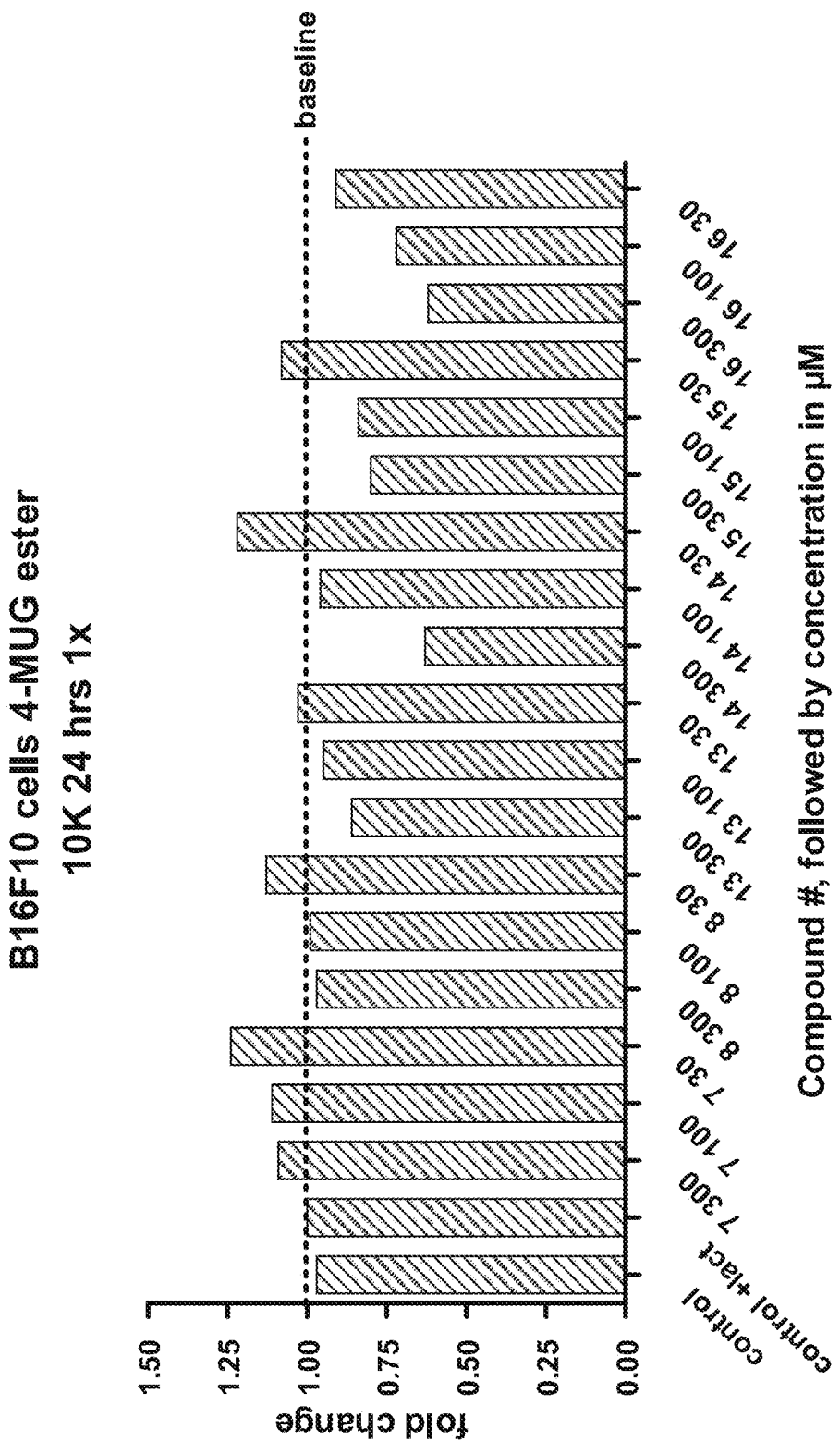
FIG. 10A is a graph showing that a dye which tags dead or dying cells, CellTag 700, is not substantially bound to B16 cells at 24 hours in the setting of treatment with embodiments of 4-MUG esters of the present disclosure, indicating that these compounds are not toxic.
Figure 10B:
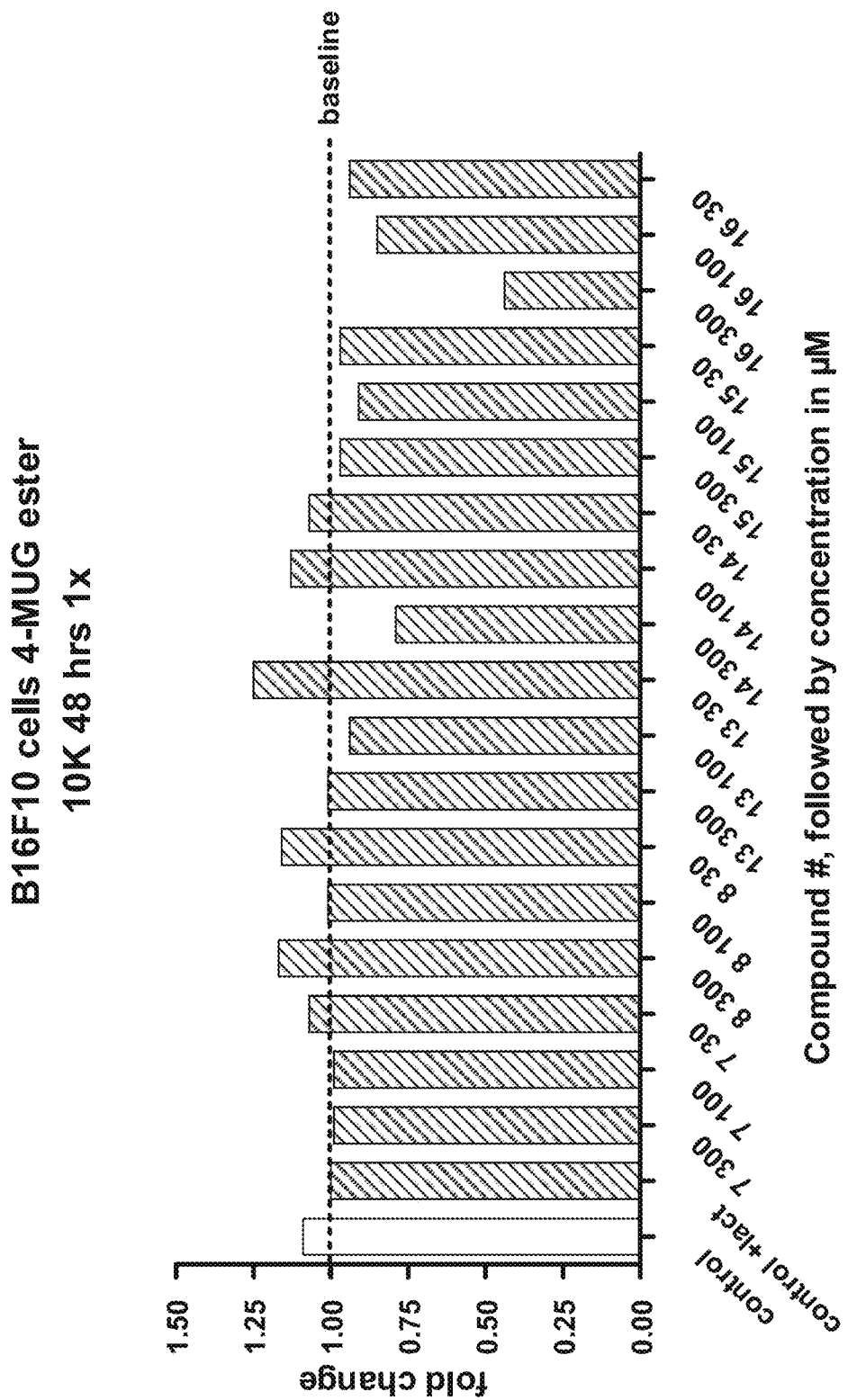
FIG. 10B is a graph showing that a dye which tags dead or dying cells, CellTag 700, is not substantially bound to B16 cells at 48 hours in the setting of treatment with embodiments of 4-MUG esters of the present disclosure, indicating that these compounds are not toxic.
Figure 10C:
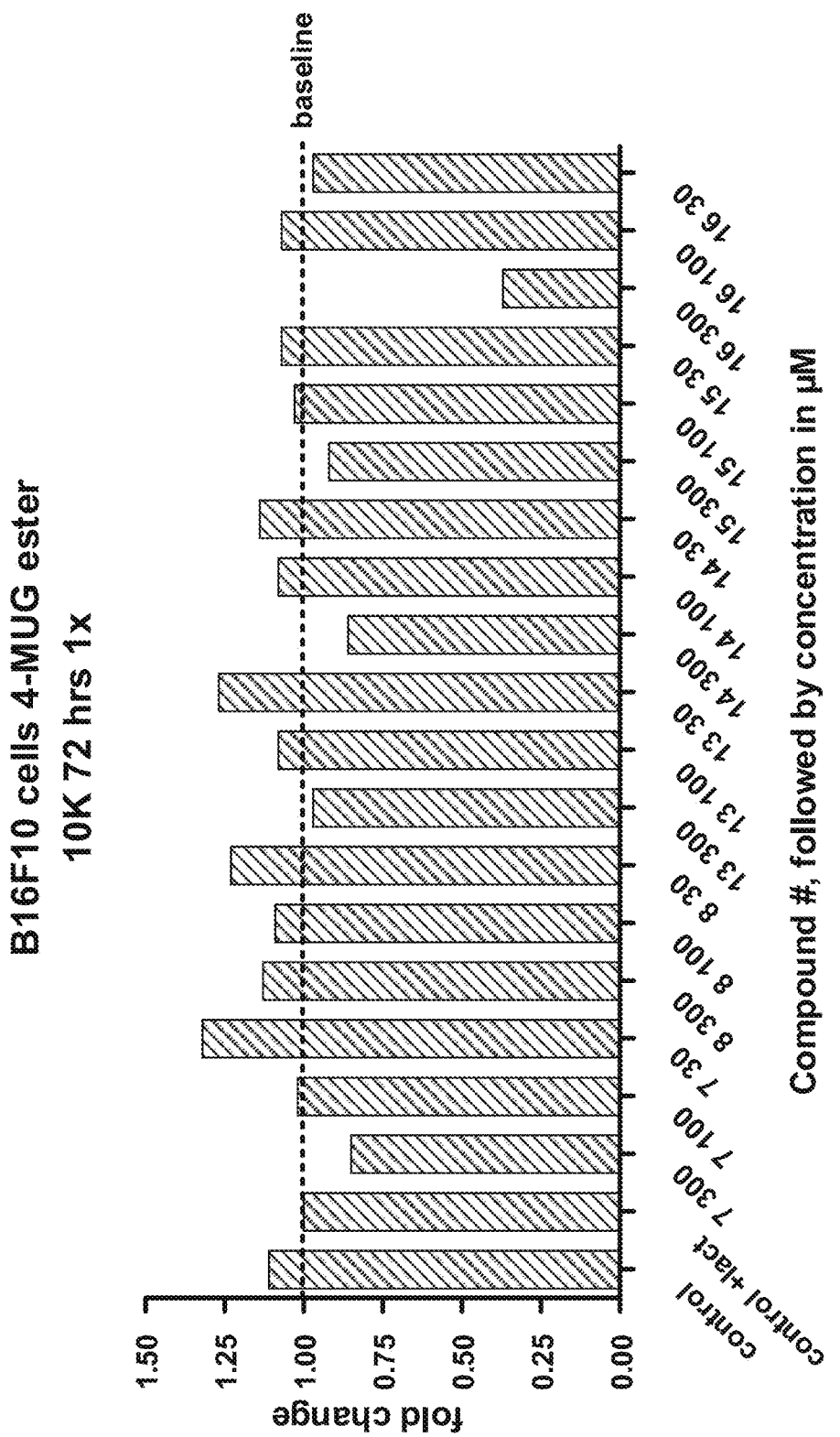
FIG. 10C is a graph showing that a dye which tags dead or dying cells, CellTag 700, is not substantially bound to B16 cells at 72 hours in the setting of treatment with embodiments of 4-MUG esters of the present disclosure, indicating that these compounds are not toxic.

A shown in FIG. 1, 4-MUG is a major metabolite of 4-MU. As will be described in EXAMPLE 1 below, 4-MUG and newly described derivatives of 4-MUG (FIG. 2) are pharmacologically active. Indeed, 4-MUG inhibits HA synthesis by human cell lines as well as 4-MU (FIGS. 3 and 4). The derivatives of 4-MUG of the present disclosure are likewise pharmacologically active (FIGS. 5-8). Not all derivatives of 4-MUG are active against HA synthesis (FIG. 9). These HA quantification results were all normalized to protein levels (FIGS. 10A-10C). This is an exciting and previously unknown finding that provides the possibility of delivering 4-MUG or 4-MUG derivatives as an agent to inhibit HA synthesis. It was previously assumed that 4-MUG was pharmacologically inactive and indeed all of the published bioavailability calculations that have been made in regards to 4-MU reflect this assumption (Garrett, E. R., et al., *Biopharm. Drug Dispos.* 14, 13-39 (1993); Garrett, E. R. and Venitz, *J Pharm Sci* 83, 115-116 (1994)).

The manner in which 4-MUG inhibits HA synthesis is unclear. Typically, glucuronidation is a metabolic step that promotes the excretion and clearance of most drugs. Indeed, because glucuronidated compounds are often more water soluble, they typically do not enter cells as well as more lipophilic parent compounds. Thus, it is surprising and not intuitive that the 4-MUG or its derivatives would inhibit HA synthesis.

It was previously reported that 4-MU promotes induction of FoxP3+ regulatory T-cells (Nagy, N. et al., *J. Clin. Invest.* 125, 10.1172/JCI79271-0 (2015); Kuipers, H. F. et al., *Proc. Natl. Acad. Sci. U.S.A.* 113, 1339-1344 (2016); Nagy, N. et al., *Front. Immunol.* 6, 123 (2015)), a critical cell type that promotes immune tolerance in multiple tissues and disease states (Sakaguchi, S., et al., *Nat. Rev. Immunol.* 10, 490-500 (2010)). In the present disclosure, it was observed that 4-MUG also has this property in vivo (FIG. 11).

In light of these data, 4-MUG and its derivatives can reduce or inhibit systemic HA synthesis and reduce or prevent inflammatory, autoimmune, allergic, or atopic disease in a subject.

Synthesis

The compounds of the present disclosure can be prepared in a variety of ways known to one skilled in the art of organic synthesis. The compounds of the present disclosure can be synthesized using the methods as hereinafter described below, together with synthetic methods known in the art of synthetic organic chemistry or variations thereon as appreciated by those skilled in the art.

The compounds of this disclosure can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art (e.g., chromatography (medium pressure) on a suitable adsorbent (e.g., silica gel, alumina and the like) HPLC, or preparative thin layer chromatography; distillation; sublimation, trituration, or recrystallization).

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene's Protective Groups in Organic Synthesis*, 4$^{th}$Ed., John Wiley & Sons: New York, 2006, which is incorporated herein by reference in its entirety.

The reactions of the processes described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the reaction step, suitable solvent(s) for that particular reaction step can be selected. Appropriate solvents include water, alkanes (such as pentanes, hexanes, heptanes, cyclohexane, etc., or a mixture thereof), aromatic solvents (such as benzene, toluene, xylene, etc.), alcohols (such as methanol, ethanol, isopropanol, etc.), ethers (such as dialkylethers, methyl tert-butyl ether (MTBE), tetrahydrofuran (THF), dioxane, etc.), esters (such as ethyl acetate, butyl acetate, etc.), halogenated solvents (such as dichloromethane (DCM), chloroform, dichloroethane, tetrachloroethane), dimethylformamide (DMF), dimethylsulfoxide (DMSO), acetone, acetonitrile (ACN), hexamethylphosphoramide (HMPA) and N-methylpyrrolidone (NMP). Such solvents can be used in either their wet or anhydrous forms.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

The compounds of the disclosure can be prepared, for example, using the reaction pathways and techniques as described below.

As an example, the carboxylic acid functionality at the 5-position of the glucuronic acid moiety in 4-methylumbelliferyl-β-glucuronide hydrate can be esterified with ethylbromide or bromobutane in the presence of a base such as 1,8-diazabicyclo[5.4.0]undec-7-ene (DBU). The esterified methylumbelliferyl-β-D-glucuronide can then be acetylated at all of the remaining hydroxyl groups with acetyl chloride in the presence of a base such as pyridine.

Starting from the 4-methylumbelliferyl-O-D-glucuronide that has been esterified at the 5-position, the 4-salicylic ester derivative of 4-methylumbelliferyl-O-D-glucuronide can be synthesized by reacting a 5-ethyl- or 5-butyl-ester of 4-methylumbelliferyl-β-D-glucuronide with sterically encumbered 2-ethoxybenzoyl chloride in the presence of a base such as pyridine.

Compositions, Dosages, Methods of Administration

In some embodiments, the present disclosure relates to a pharmaceutical composition including one or more physiologically acceptable surface active agents, additional carriers, diluents, excipients, smoothing agents, suspension agents, film forming substances, and coating assistants, or a combination thereof; and a compound or composition disclosed herein. Acceptable additional carriers or diluents for therapeutic use are well known in the pharmaceutical art, and are described, for example, in *Remington's Pharmaceutical Sciences,* 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical compounds described herein can be administered to a subject such as a human patient per se, or in pharmaceutical compositions where they are mixed with other active ingredient(s), as in combination therapy, or, for example with suitable carriers or excipient(s). In some embodiments, a dosage form includes those forms in which the compound is administered per se. In addition, a dosage form may include a pharmaceutical composition. In any case, the dosage form may comprise a sufficient amount of the compound to treat the disease as part of a particular administration protocol, as would be understood by those of skill in the art. Techniques for formulation and administration of the compounds of the instant application may be found in *Remington's Pharmaceutical Sciences*, Mack Publishing Co., Easton, Pa., 18th edition, 1990.

The mode of administration can be any medically acceptable mode including oral administration, sublingual administration, intranasal administration, intratracheal administration, inhalation, ocular administration, topical administration, transdermal administration, intradermal administration, rectal administration, vaginal administration, subcutaneous administration, intravenous administration, intramuscular administration, intraperitoneal administration, intrasternal, administration, or via transmucosal administration. In addition, modes of administration can be via an extracorporeal device and/or tissue-penetrating electro-magnetic device.

The particular mode selected will depend upon the particular compound selected, the desired results, the particular condition being treated and the dosage required for therapeutic efficacy. The methods described herein, generally speaking, can be practiced using any mode of administration that is medically acceptable, for example, any mode that produces a response without causing clinically unacceptable adverse effects.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound can also be administered in sustained or controlled release dosage forms, including depot injections, osmotic pumps, pills, transdermal (including electrotransport) patches, and the like, for prolonged and/or timed, pulsed administration at a predetermined rate. In addition, modes of administration can be via an extracorporeal device and/or tissue-penetrating electro-magnetic device.

The pharmaceutical compositions may be manufactured in a manner that is itself known, e.g., by means of conventional mixing, dissolving, granulating, dragee-making, levigating, emulsifying, encapsulating, entrapping or tableting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g. in *Remington's Pharmaceutical Sciences*, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the composition can be formulated readily by combining the compositions of interest with pharmaceutically acceptable carriers well known in the art. Such carriers, which may be used in addition to the cationic polymeric carrier, enable the compositions to be formulated as tablets, pills, dragees, capsules, liquids, gels, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), e.g., Povidone. If desired, disintegrating agents may be added, such as the cross-linked polyvinylpyrrolidone (e.g. Crospovidone), agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner. Administration to the buccal mucosa and sublingually are contemplated.

For administration by inhalation, the composition can be conveniently delivered in the form of an aerosol spray presentation from pressurized packs or a nebulizer, with the use of a suitable propellant, e.g., dichlorodifluoro methane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Such suitable pharmaceutical formulations are most often formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in *Remington's Pharmaceutical Sciences*, 18th Ed., Mack Publishing Co., Easton, Pa. (1990), which is incorporated herein by reference in its entirety, and well-known to those skilled in the art, suitable formulations are most often isotonic, slightly buffered to maintain a pH of 5.5 to 6.5, and most often include antimicrobial preservatives and appropriate drug stabilizers. Pharmaceutical formulations for intraauricular delivery include suspensions and ointments for topical application in the ear. Common solvents for such aural formulations include glycerin and water.

The compositions may also be formulated in rectal compositions such as suppositories or retention enemas, e.g. containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a co-solvent system comprising benzyl alcohol, a nonpolar surfactant, a water-miscible organic polymer, and an aqueous phase. A common co-solvent system used is the VPD co-solvent system, which is a solution of 3% w/v benzyl alcohol, 8% w/v of the nonpolar surfactant Polysorbate80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g. polyvinyl pyrrolidone; and other sugars or polysaccharides may substitute for dextrose.

Methods for treating for example, PSC may include administering a therapeutically effective amount of the therapeutic compounds as described herein. Preventing a disease may include prophylactically administering the therapeutic compounds to prevent symptoms of the disease, or spread of a disease in a subject at imminent risk of developing the disease.

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the active compound into contact with living tissue.

Pharmaceutical compositions suitable for administration include compositions where the active ingredients are contained in an amount effective to achieve its intended purpose. In some embodiments, a therapeutically effective amount of a compound is an amount effective to treat a disease herein, for example, in a mammalian subject (e.g., a human). The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 10 mg/g body weight, such as about 100 microgram/g to about 10 mg/g body weight, for example, about 3-50 mg/kg, about 10-25 mg/kg, about 1-100 mg/kg, or about 0.1-10 mg/kg. Alternatively dosages may be based and calculated upon the surface area of the patient, as understood by those of skill in the art. The exact formulation, route of administration and dosage for the pharmaceutical compositions can be chosen by the individual physician in view of the patient's condition. (See e.g., Fingl et al. 1975, in *The Pharmacological Basis of Therapeutics*, which is hereby incorporated herein by reference in its entirety, with particular reference to Ch. 1, p. 1). In some embodiments, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, such as about 25% to about 250% of the established human dosage may be used. Where no human dosage is established, as will be the case for newly-discovered pharmaceutical compositions, a suitable human dosage can be inferred from appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 5000 mg of the active ingredient, such as about 500 mg to about 3000 mg, e.g. 900-1800 or 900-2700 mg/day. 4-MU is approved for treatment of biliary dyskinesia in the EU, at doses of 1800 mg per day. 4-MU is extracted by the liver and concentrated in the biliary tract. However, it appears to be safe at higher doses than that. Due to the poor bioavailability of 4-MU by oral delivery, oral doses for treating PSC will be equivalent to the high end of the EU approved range, or higher. 4-MU is currently available in 300 mg tablets. Dosing 1800 mg requires 2 300 mg tablets, three times per day. A higher dose oral form (e.g. 600 mg, 1000 mg, or 1200 mg) would be valuable. In other embodiments, an intravenous, sublingual, intranasal, subcutaneous, intramuscular or inhalation dose of the active ingredient of about 0.01 mg to about 2000 mg, such as about 10 mg to about 1000 mg, such as 10 mg to 250 mg or 50 mg to 100 mg is used. In cases of administration of a pharmaceutically acceptable salt, dosages may be calculated as the free acid. In some embodiments, the composition is administered 1 to 4 times per day. Alternatively the compositions may be administered by continuous intravenous infusion, such as at a dose of up to about 1-1000, 3-500, or 10-50 mg/day. As will be understood by those of skill in the art, in certain situations it may be necessary to administer the compounds disclosed herein in amounts that exceed, or even far exceed, the above-stated, dosage range in order to effectively and aggressively treat particularly aggressive diseases. In some embodiments, the compounds will be administered for a period of continuous therapy, for example for a week or more, or for months or years.

Dosage amount and interval may be adjusted individually to provide plasma levels of the active moiety which are sufficient to maintain the desired effects. HPLC assays or bioassays can be used to determine plasma concentrations.

In cases of local administration or selective uptake, the effective local concentration of the drug may not be related to plasma concentration.

The amount of composition administered may be dependent on the subject being treated, on the subject's weight, the severity of the disease, the manner of administration and the judgment of the prescribing physician.

Compositions disclosed herein can be evaluated for efficacy and toxicity using known methods. For example, the toxicology of the compound may be established by determining in vitro toxicity towards a cell line, such as a mammalian, and such as a human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound formulated in a compatible pharmaceutical carrier may also be prepared, placed in an appropriate container, and labeled for treatment of an indicated condition.

In some embodiments, in the pharmaceutical industry, it is standard practice to provide substantially pure material when formulating pharmaceutical compositions. Therefore, in some embodiments, "substantially pure" refers to the amount of purity required for formulating pharmaceuticals, which may include, for example, a small amount of other material that will not affects the suitability for pharmaceutical use. In some embodiments, the substantially pure compound contains at least about 96% of the compound by weight, such as at least about 97%, 98%, 99%, or 100% of the compound.

The terms "approximately, "about," and "substantially" as used herein represent an amount close to the stated amount that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

In some embodiments, the present disclosure provides compositions that include the compounds of the disclosure. The compositions include one or more compounds of the disclosure, optionally one or more additional therapeutic agents, and a medium (e.g., a lipophilic medium). Representative lipophilic medium includes the following:

Fatty acids and esters thereof, including carboxylic acids of various chain lengths, mostly straight chain, but which could be branched, examples of which include capric, caprylic, caproic, lauric, myristic, stearic, oleic, linoleic, behenic, and as well as saturated or unsaturated fatty acids and esters;

Fatty acids esterified with glycerin to form mono-, di-, or triglycerides, which can be synthetic or derived from natural sources, including, but not limited to, for example, glycerides such as soybean oil, cottonseed oil, rapeseed oil, fish oil, castor oil, Capmul® MCM, Captex® 300, Miglyol® 812, glyceryl monooleate, triacetin, acetylated monoglyceride, tristearin, glyceryl behenate, and diacetyl tartaric acid esters of monoglycerides;

Glycerides conjugated to other moieties, such as polyethylene glycol (for example, Labrasol®, Labrafac™, Cremophor® EL);

Phospholipids, either natural or synthetic, such as dimyristyl phosphatidylcholine, egg lecithin, and pegylated phospholipids;

Other fatty esters including fatty alcohols (myristyl myristate, isopropyl palmitate), or sugars (sorbitan monooleate, SPAN® 80, Tween 80, sucrose laurate);

Fatty alcohols such as stearyl alcohol, lauryl alcohol, benzyl alcohol, or esters or ethers thereof, such as benzyl benzoate;

Organic co-solvents can also be used in the compositions, optionally in combination with water, including for example, ethanol, polyethylene glycol, propylene glycol, glycerol, N-methyl pyrrolidone, and dimethyl sulfoxide.

Emulsion, Microemulsion, and Micelle Formulations

In a further aspect, the disclosure provides emulsion, microemulsion, and micelle formulations that include a compound of the disclosure. Methods for making the emulsion, microemulsion, and micelle formulations are also provided.

As used herein, the term "emulsion" refers to a colloidal dispersion of two immiscible liquids, such as an oil and water, in the form of droplets, whose diameter, in general, are between 0.1 and 3.0 microns and which is typically optically opaque, unless the dispersed and continuous phases are refractive index matched. Such systems possess a finite stability, generally defined by the application or relevant reference system, which can be enhanced by the addition of amphiphilic molecules or viscosity enhancers.

The term "microemulsion" refers to a thermodynamically stable isotropically clear dispersion of two immiscible liquids, such as an oil and water, stabilized by an interfacial film of surfactant molecules. The microemulsion has a mean droplet diameter of less than 200 nm, in general between 10-50 nm. In the absence of water, mixtures of oil(s) and non-ionic surfactant(s) form clear and isotropic solutions that are known as self-emulsifying drug delivery systems (SEDDS) and can be used to improve lipophilic drug dissolution and oral absorption.

The emulsion and microemulsion formulations include an oil phase and an aqueous phase. The emulsion or microemulsion can be an oil-in-water emulsion or a water-in-oil emulsion. The oil phase includes one or more compounds of the disclosure and a lipophilic medium, as described above. In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.5 weight percent based on the total weight of the formulation. In one embodiment, the lipophilic medium is present in the formulation in an amount from about 2 to about 20 weight percent based on the total weight of the formulation. In one embodiment, the lipophilic medium is present in the formulation in an amount from about 4 to about 12 weight percent based on the total weight of the formulation. In one embodiment, the lipophilic medium is present in the formulation in an amount from about 6 to about 10 weight percent based on the total weight of the formulation.

In addition to the compounds of the disclosure, the emulsion or microemulsion formulations can include other components commonly used in emulsions and microemulsions, and particularly used in pharmaceutical emulsions and microemulsions. These components include surfactants and co-solvents, among others.

Suitable nonionic surfactants include block copolymers of ethylene oxide and propylene oxide known as POLOXAMERS or PLUROINICS®. These synthetic block copolymers of having the general structure: $H(OCH_2CH_2)_a(OC_3H_6CH_2)_b(OCH_2CH_2)_aOH$. The following variants based on the values of a and b are commercially available from BASF Performance Chemicals (Parsippany, N.J.) under the trade name PLURONIC® and consist of the group of surfactants designated by the CTFA name of POLOXAMER 108, 188, 217, 237, 238, 288, 338, 407, 101, 105, 122, 123, 124, 181, 182, 183, 184, 212, 231, 282, 331, 401, 402, 185, 215, 234, 235, 284, 333, 334, 335, and 403. For the most commonly used POLOXAMERS 124, 188, 237, 338, and 407 the values of a and b are 12/20, 79/28, 64/37, 141/44 and 101/56, respectively. In one embodiment the nonionic surfactant is present in the formulation in an amount from about 0.5 to about 5 weight percent based on the total weight of the formulation.

Co-solvents useful in the formulations include ethanol, polyethylene glycol, propylene glycol, glycerol, N-methylpyrrolidone, dimethylamide, and dimethylsulfoxide, among others. Polyethylene glycol (PEG) is a hydrophilic, polymerized form of ethylene glycol, consisting of repeating units having the chemical structure: $(-CH_2CH_2O-)$. The general formula for polyethylene glycol is $H(OCH_2CH_2)_nOH$. The molecular weight ranges from 200 to 10,000. Such various forms are described by their molecular weights, for example, PEG-200, PEG-300, PEG-400, and the like.

In a further aspect, the disclosure provides micelle formulations that include a compound of the disclosure and an aqueous phase. Micelles are organized aggregates of one or more surfactants in solution. In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.0 weight percent based on the total weight of the formulation. Suitable surfactants include those noted above, and in the amounts noted above.

The micelle formulation can also include additional components such as co-solvents including those noted above. In one embodiment, the micelle formulation includes a polyethylene glycol and a lower alkyl alcohol (e.g., ethanol). In one embodiment, the co-solvents are present in an amount from about 2 to about 20 weight percent based on the total weight of the formulation. The micelle, emulsion, and microemulsion formulations include an aqueous phase. In one embodiment, the aqueous phase includes deionized water. In another embodiment, the aqueous phase includes saline. In another embodiment, the aqueous phase is saline buffered with an organic acid (e.g., succinate, citrate).

The disclosure also provides the use of the compounds of the disclosure in the manufacture of a medicament, for example, for the treatment of cell proliferative disease.

In other aspects, methods for administering a compound of the disclosure to a subject in need thereof, and methods for treating a condition treatable by administration of a therapeutically effective amount of a compound of the disclosure are also provided. These methods include the administration of the compounds, compositions, emulsion formulations, microemulsion formulations, and micelle formulations described herein.

In one embodiment, the disclosure provides a method for treating a condition that is treatable by the parent, unmodified nucleoside or nucleoside analogue (e.g., a cell proliferative disease such as cancer). In the method, a therapeutically effective amount of a compound of the disclosure is administered to a subject in need thereof.

In one embodiment, the disclosure provides a method for intracellular delivery of a monophosphorylated nucleoside or nucleoside analogue. In the method, a compound of the disclosure is contacted with a cell. When internalized into a cell, the compound is cleaved by cellular enzymes (e.g., phosphatase and/or phosphodiesterase) into the corresponding nucleoside or nucleoside analogue phosphate, and tocopherol or tocotrienol.

In one embodiment, the disclosure provides a method for treating a cell proliferative disease by administering a compound of the disclosure having a nucleoside or nucleoside analogue derived from a therapeutic drug effective in treating cell proliferative disease. Representative cell proliferative diseases treatable by the compounds of the disclosure include hematologic cancers, such as leukemia, lymphoma, and myeloma; and nonhematologic cancers, such as solid tumor carcinomas (e.g., breast, ovarian, pancreatic, colon, colorectal, lung (e.g., non-small cell lung), and bladder), sarcomas, and gliomas.

Therapeutically effective amounts of the compounds will generally range up to the maximally tolerated dosage, but the concentrations are not critical and can vary widely. The precise amounts employed by the attending physician will vary, of course, depending on the compound, route of administration, physical condition of the patient and other factors. The daily dosage can be administered as a single dosage or can be divided into multiple doses for administration.

The amount of the compound actually administered will be a therapeutically effective amount, which term is used herein to denote the amount needed to produce a substantial beneficial effect. Effective doses can be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the compounds of the disclosure can be determined by standard pharmaceutical procedures, in cell cultures or experimental animals (e.g., ED50, the dose therapeutically effective in 50% of the population; and LD50, the dose lethal to 50% of the population). The dose ratio between therapeutic and toxic effects is the therapeutic index, and it can be expressed as the ratio LD50 to ED50. Modified therapeutic drug compounds that exhibit large therapeutic indices are particularly suitable in the practice of the methods of the disclosure. The data obtained from cell culture assays and animal studies can be used in formulating a range of dosage for use in humans or other mammals. The dosage of such compounds lies preferably within a range of circulating concentrations that include the ED50 with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The compounds of the disclosure can be administered alone, or in combination with one or more additional therapeutic agents. Appropriate amounts in each case will vary with the particular agent, and will be either readily known to those skilled in the art or readily determinable by routine experimentation.

Administration of the compounds of the disclosure is accomplished by any effective route, for example, parenteral, topical, or oral routes. Methods of administration include inhalational, buccal, intramedullary, intravenous, intranasal, intrarectal, intraocular, intraabdominal, intraarterial, intraarticular, intracapsular, intracervical, intracranial, intraductal, intradural, intralesional, intramuscular, intralumbar, intramural, intraocular, intraoperative, intraparietal, intraperitoneal, intrapleural, intrapulmonary, intraspinal, intrathoracic, intratracheal, intratympanic, intrauterine, intravascular, and intraventricular administration, and other conventional means. The compounds of the disclosure having anti-tumor activity can be injected directly into a tumor, into the vicinity of a tumor, into a blood vessel that supplies blood to the tumor, or into lymph nodes or lymph ducts draining into or out of a tumor.

The emulsion, microemulsion, and micelle formulations of the disclosure can be nebulized using suitable aerosol propellants that are known in the art for pulmonary delivery of the compounds.

The compounds of the disclosure can be formulated into a composition that additionally comprises suitable pharmaceutically acceptable carriers, including excipients and other compounds that facilitate administration of the compound to a subject. Further details on techniques for formulation and administration can be found in the latest edition of "Remington's Pharmaceutical Sciences" (Maack Publishing Co., Easton, Pa.).

Oral Compositions

Compositions for oral administration can be formulated using pharmaceutically acceptable carriers well known in the art, in dosages suitable for oral administration. Such carriers enable the compositions containing the compounds of the disclosure to be formulated as tablets, pills, dragees, capsules, liquids, gels, syrups, slurries, suspensions, suitable for ingestion by a subject. Compositions for oral use can be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins, such as gelatin and collagen. If desired, disintegrating or solubilizing agents can be added, such as the crosslinked polyvinyl pyrrolidone, agar, alginic acid, or a salt thereof, such as sodium alginate.

Dragee cores are provided with suitable coatings such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound (i.e., dosage).

Compounds for oral administration can be formulated, for example, as push-fit capsules made of gelatin, as well as soft, sealed capsules made of gelatin and a coating such as glycerol or sorbitol. Push-fit capsules can contain the compounds mixed with filler or binders such as lactose or starches, lubricants such as talc or magnesium stearate, and, optionally, stabilizers. In soft capsules, the covalent conjugates can be dissolved or suspended in suitable liquids, such as fatty oils, liquid paraffin, or liquid polyethylene glycol with or without stabilizers.

Topical, Nasal, Rectal Compositions

For topical or nasal administration, penetrants appropriate to the particular barrier to be permeated are typically used in the formulation. Examples of these are 2-pyrrolidone, N-methyl-2-pyrrolidone, dimethylacetamide, dimethyl-formamide, propylene glycol, methyl or isopropyl alcohol, dimethyl sulfoxide, and azone. Additional agents can further be included to make the formulation cosmetically acceptable. Examples of these are fats, waxes, oils, dyes, fragrances, preservatives, stabilizers, and surface-active agents. Keratolytic agents such as those known in the art can also be included. Examples are salicylic acid and sulfur. For topical administration, the composition can be in the form of a transdermal ointment or patch for systemic delivery of the compound and can be prepared in a conventional manner (see, e.g., Barry, Dermatological Formulations (Drugs and the Pharmaceutical Sciences—Dekker); Harry's Cosmeticology (Leonard Hill Books).

For rectal administration, the compositions can be administered in the form of suppositories or retention enemas. Such compositions can be prepared by mixing the compounds with a suitable non-irritating excipient that is solid at ordinary temperatures but liquid at the rectal temperature and will therefore melt in the rectum to release the drug. Suitable excipients include, but are not limited to, cocoa butter and polyethylene glycols.

The amounts of each of these various types of additives will be readily apparent to those skilled in the art, optimal amounts being the same as in other, known formulations designed for the same type of administration.

Composition Manufacture

Compositions containing the compounds of the disclosure can be manufactured in a manner similar to that known in the art (e.g., by means of conventional mixing, dissolving, granulating, dragee-making, levigating, emulsifying, encapsulating, entrapping or lyophilizing processes). The compositions can also be modified to provide appropriate release characteristics, sustained release, or targeted release, by conventional means (e.g., coating). As noted above, in one embodiment, the compounds are formulated as an emulsion.

Compositions containing the compounds can be provided as a salt and can be formed with many acids, including but not limited to hydrochloric, sulfuric, acetic, lactic, tartaric, malic, and succinic. Salts tend to be more soluble in aqueous or other protonic solvents than are the corresponding free base forms.

After compositions formulated to contain a compound and an acceptable carrier have been prepared, they can be placed in an appropriate container and labeled for use. Thus, in another aspect, the disclosure provides kits.

As will be shown in EXAMPLE 1 below, an oral drug that promotes Treg induction in vivo is demonstrated. 4-MUG and its pro-drugs could be a powerful tool to promote immune tolerance. Inhibition of HA synthesis can be an effective strategy to treat inflammation. HA is an inflammatory mediator that is not currently targeted pharmacologically. 4-MUG can be a potential treatment for other autoimmunity, cancer metastasis, and other indications. HA deposits are present in multiple chronic inflammatory diseases, including multiple sclerosis, rheumatoid arthritis, juvenile idiopathic arthritis (Yoshioka, Y. et al., *Arthritis Rheum.* 65, 1160-1170 (2013)) and lupus nephritis (Yung S., et al., *Hindawi* 2012, 207190-9 (2012)). EXAMPLE 2 below shows that embodiments of the compounds of the present disclosure, such as butyl-4-MUG, surprisingly delays the onset of diabetes at 1/100$^{th}$ the dose of 4-MU. EXAMPLE 3 below shows the synthesis of embodiments of compounds of the present disclosure. EXAMPLE 4 below describe the treatment of PSC using 4-MU.

EXAMPLE 1

Treg Induction In Vivo by 4-MUG and 4-MUG Prodrugs
  B16F10 Cells
  B16F10 is a murine melanoma cell line. The cells are adherent and the cell morphology shows a mixture of spindle-shaped and epithelial-like cells. The cells were cultured at 37° C. temperature and an atmosphere of 95% air and 5% carbon dioxide. Cells were cultured in DMEM plus 10% FBS.

For the 4-MUG ester experiments, cells were seeded in 48-well plates, at a density of 10,000 cells per well and cultured for 24-72 hours. 4-MU, 4-MUG and the 4-MUG esters were diluted 1:1000 from their stock concentration and added to the cell medium in their final µM concentrations.

For the analysis, the cells and the cell supernatant were collected at the end of each experiment and stored at −20° C. until further use.

Cell Lysis 48-well plates from previous experiments were thawed and 200 µL cell lysis buffer was added to each well. Cells were incubated for 15 minutes at room temperature. The whole lysate was transferred into a 96-well v-bottom plate and centrifuged at 3500 g for 20 minutes at 4° C. After spinning 25 µL from each well was transferred into a flat-bottom 96-well plate and stored until further use. Cell lysis buffer contains Tris-HCl, EDTA, SDS, $MgCl_2$ and Super Nucleasis®.

Protein Measurement

Protein measurement was performed by using the Pierce BCA Protein Assay Kit® (Thermo Scientific) according to the manufacturer instructions. The BCA Protein assay is based on bicinchoninic acid (BCA) for the colorimetric detection and quantitation of total protein. This method combines a biuret reaction (reduction of $Cu2+$ to $Cu1+$ by protein in an alkaline medium) with a highly and selective colorimetric detection of the cuprous cation ($Cu1+$) with the help of bicinchoninic acid. A purple-colored reaction product is formed by the chelation of two BCA molecules with one cuprous ion. This complex has a strong absorbance at 562 nm.

LI-COR CellTag™ 700 Cell Number Normalization

The CellTag 700 stain is a near-infrared fluorescent, non-specific cell stain that provides accurate normalization to cell number. The stain accumulates in both the nucleus and cytoplasm of permeabilized cells, and provides linear fluorescent signal across a wide range of cell types and cell numbers. CellTag 700 is detected in the 700 nm channel of the Odyssey® Imaging System.

Cells were fixed with 4% formaldehyde for 30 minutes at room temperature and afterwards permeabilized with 0.1% Triton X-100 in PBS. Cells were washed five times with PBS and 0.1% Tween 20. Subsequently 0.2 uM CellTag 700 stain was added to the cells for 60 min. Cells were washed again with PBS containing 0.1% Tween 20 five times for 5 minutes. Next the plate was scanned in the 700 nm channel of the Odyssey Infrared Imaging System.

Hyaluronan (HA) ELISA

The identification of HA in the samples is achieved by utilizing a highly specific HA binding protein (HABP) probe that interacts with HA. The HABP is prepared by enzymatic digestion of the chondroitin sulfate proteoglycan aggrecan present in bovine nasal cartilage. The HA concentration in the tissue is determined by using an ELISA-like assay.

96-well plates were coated with HA-BSA for 1 hour at room temperature. Samples and standards were prepared with HABP for the assay. The plate was washed after coating three times with PBS, and blocked with 10% FBS in PBS for 1 hour at room temperature. The plate was washed after blocking again with three times PBS, subsequently standards and samples were transferred onto the plate for 1 hour. The plate was washed after sample transfer four times with nanopure water. Afterwards the plate was incubated with Streptavidin-HRP for 20 minutes and washed four times with nanopure water. After washing the plate was incubated with TMB substrate for 5-20 minutes, time depending on the intensity of the developing color. In order to stop the TMB reaction, sulfuric acid was applied to the plate. The plate was read at 405 nm and the concentrations were calculated according to the standards.

Cell Staining

B16 cells were stained for phalloidin and the nuclei were visualized with DAPI. Phalloidin was used to visualize the distribution of F-actin, and DAPI was used to visualize the nuclei. Unlike the usual antibodies, DAPI emits a blue fluorescence upon binding to AT regions of DNA.

The cells were fixed with 4% formaldehyde for 20 minutes at room temperature. After fixation cells were washed three times for 5 minutes in PBS and permeabilized with 0.1% Triton X in PBS for 2 minutes. After permeabilization cells were washed again and subsequently stained for F-actin and nuclei. Cells were stained with a 50 µg/mL phalloidin solution in PBS for 40 minutes at room temperature. The staining solution was removed and the cells were washed three times for 5 minutes with PBS. Nuclei were stained for 2 minutes with a 300 nM DAPI solution, the staining solution was removed and the cells were washed three times for 5 minutes with PBS. The whole staining process was carried out protected from light.

4-MUG and newly described derivatives of 4-MUG (FIG. 2) are pharmacologically active. Indeed, 4-MUG inhibits HA synthesis by human cell lines as well as 4-MU (FIGS. 3 and 4). The derivatives of 4-MUG of the present disclosure are likewise pharmacologically active (FIGS. 5-8). Not all derivatives of 4-MUG are active against HA synthesis (FIG. 9). These HA quantification results were all normalized to protein levels using LI-COR CellTag™ 700 cell number normalization in B16 cells after exposure to 4 MUG ester. FIGS. 10A-10C shows that a dye which tags dead or dying cells, CellTag 700, is not substantially bound to B16 cells in the setting of treatment with these esters, indicating that these compounds are not toxic. Taken together, this is an exciting and previously unknown finding that provides the possibility of delivering 4-MUG or 4-MUG derivatives as an agent to inhibit HA synthesis.

The manner in which 4-MUG inhibits HA synthesis is unclear. Typically, glucuronidation is a metabolic step that promotes the excretion and clearance of most drugs. Indeed, because glucuronidated compounds are often more water soluble, they typically do not enter cells as well as more lipophilic parent compounds. Thus, it is surprising and not intuitive that the 4-MUG or its derivatives would inhibit HA synthesis.

It was previously reported that 4-MU promotes induction of FoxP3+ regulatory T-cells (Nagy, N. et al., *J. Clin. Invest.* 125, 10.1172/JCI79271-0 (2015); Kuipers, H. F. et al., *Proc. Natl. Acad. Sci. U.S.A.* 113, 1339-1344 (2016); Nagy, N. et al., *Front Immunol.* 6, 123 (2015)), a critical cell type that promotes immune tolerance in multiple tissues and disease states (Sakaguchi, S., et al., *Nat. Rev. Immunol.* 10, 490-500 (2010)). In the present disclosure, it was observed that 4-MUG also has this property in vivo. FIGS. 11A-11D graphically represent the induction of FoxP3+ regulatory T-cells by 4-MUG. 4-MUG does not increase the numbers of CD3+ T-cells (FIG. 11A), CD4+ T-cells (FIG. 11B), or CD25+ T-cells (FIG. 11C) but does increase the fraction of Foxp3+ regulatory T-cells (FIG. 11D). This indicates a specific effect on Foxp3+T regulatory T-cells.

Figure 12B:
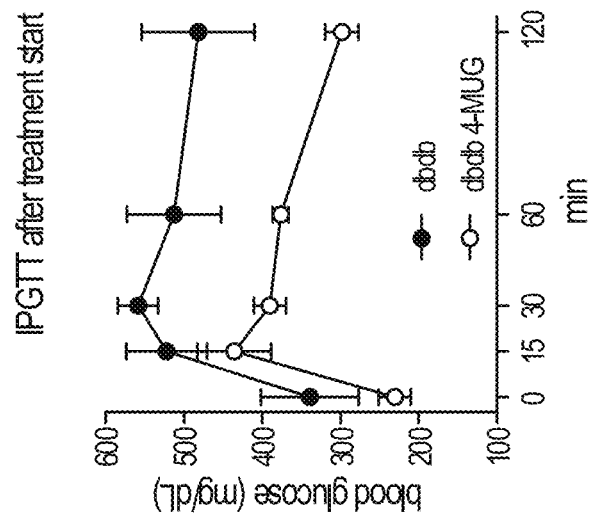
FIG. 12B graphically represents a blood glucose level over time in subjects following an intra-peritoneal glucose tolerance test (IPGTT).
Figure 12A:
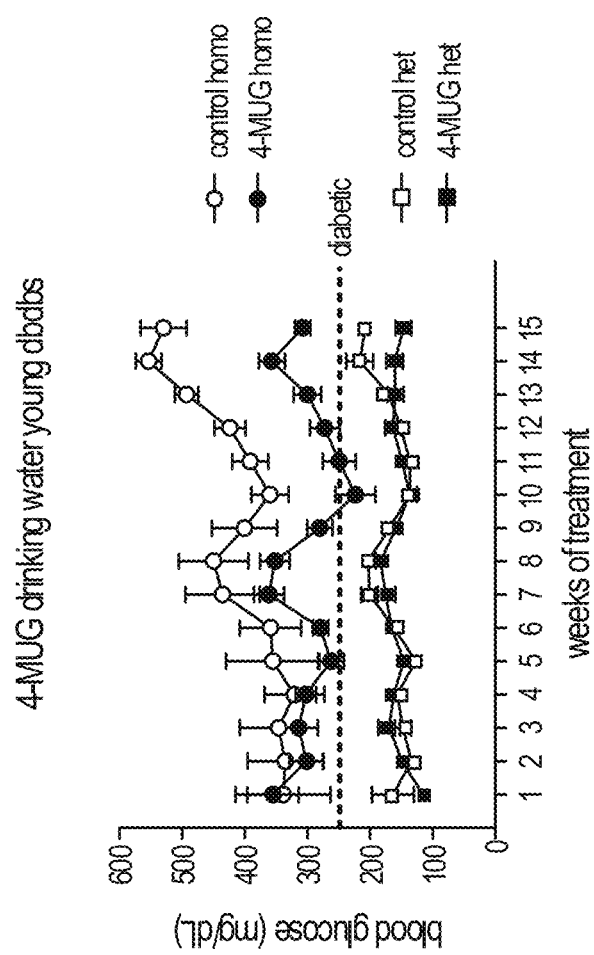
FIG. 12A graphically represents a blood glucose level over time in subjects administered 4-MUG.
Figure 13:
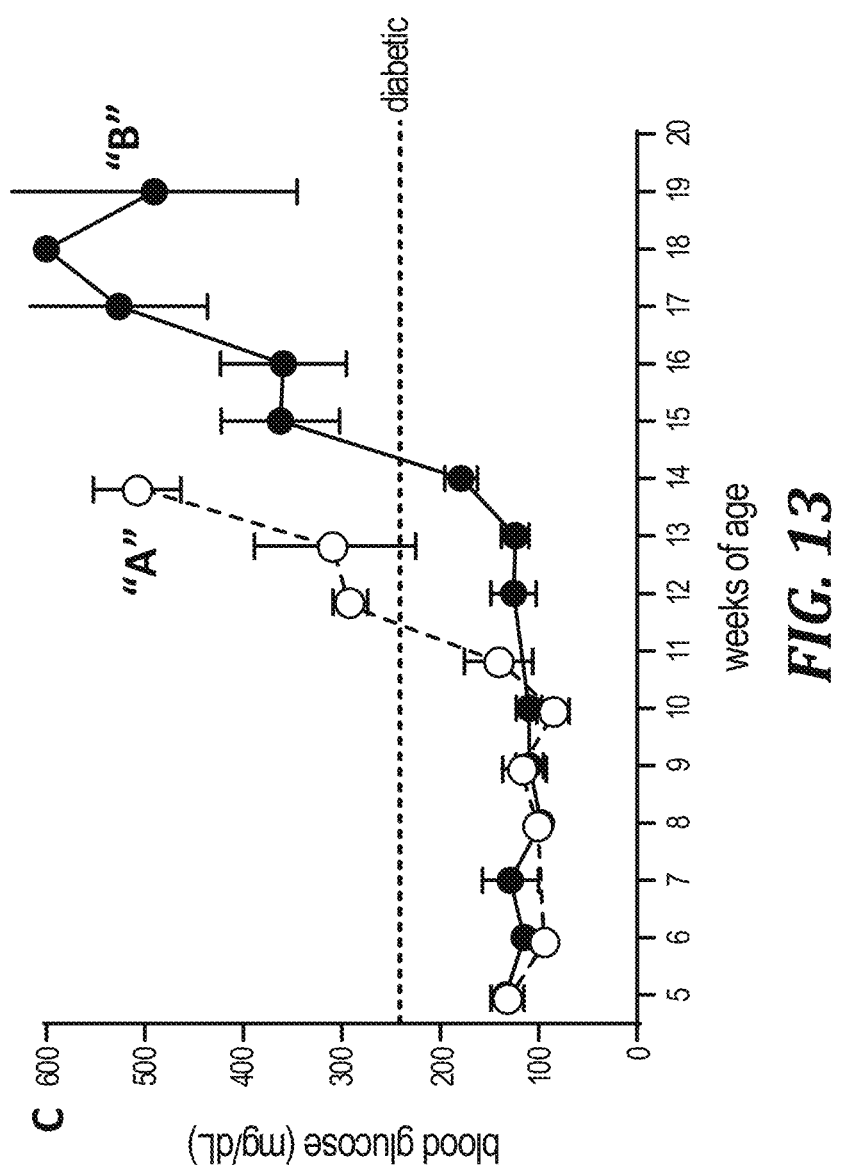
FIG. 13 is a graph showing onset of diabetes (above horizontal line at about 250 mg/dL blood glucose) in compound A or compound B-administered mice.
Figure 14A:
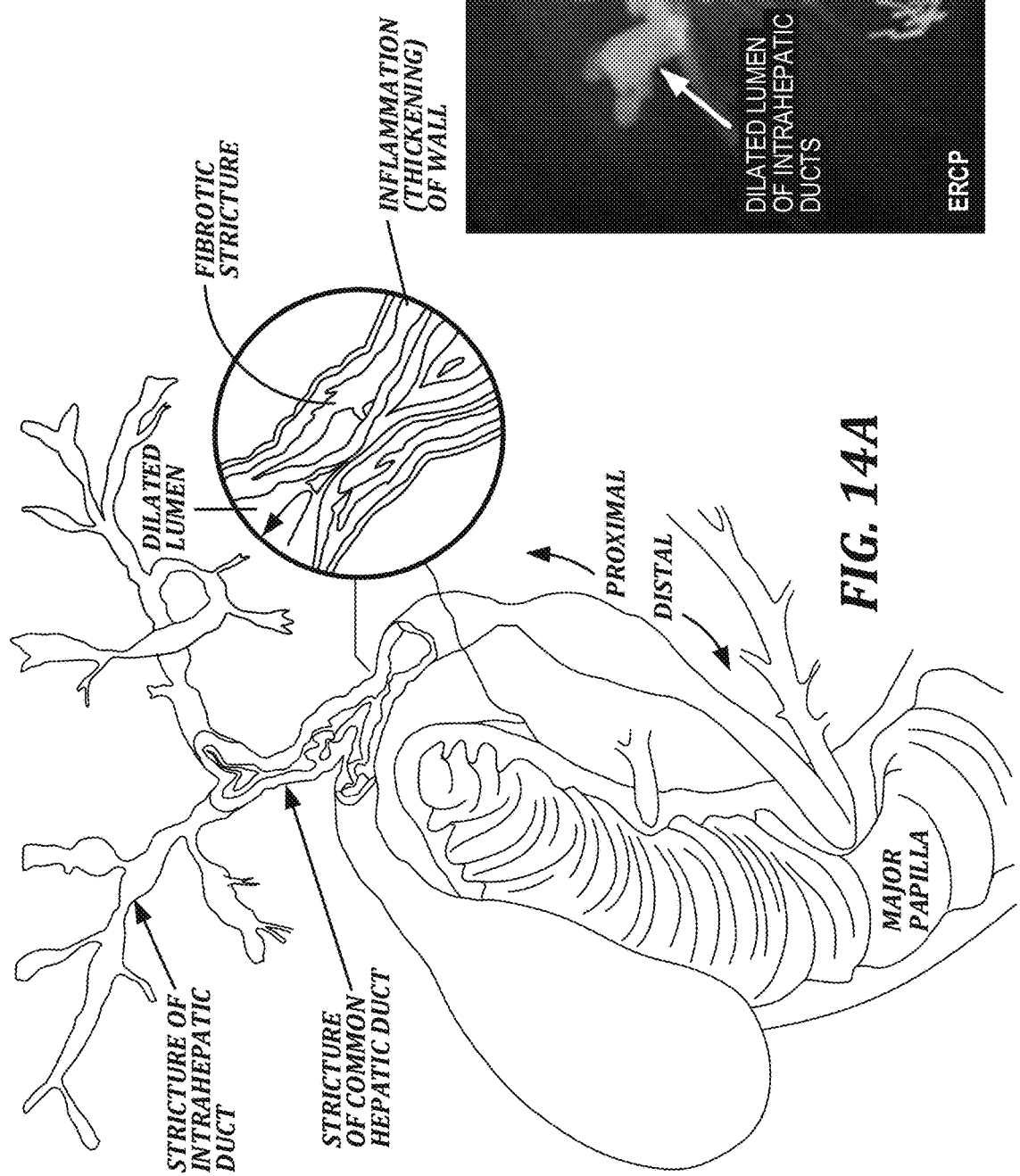
FIGS. 14A and 14B are illustrations of strictures in PSC.
Figure 14B:
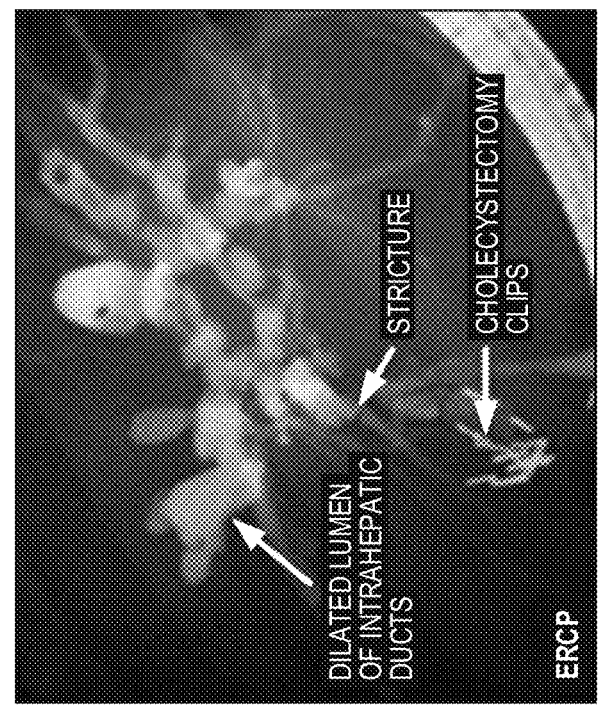
Figure 15:
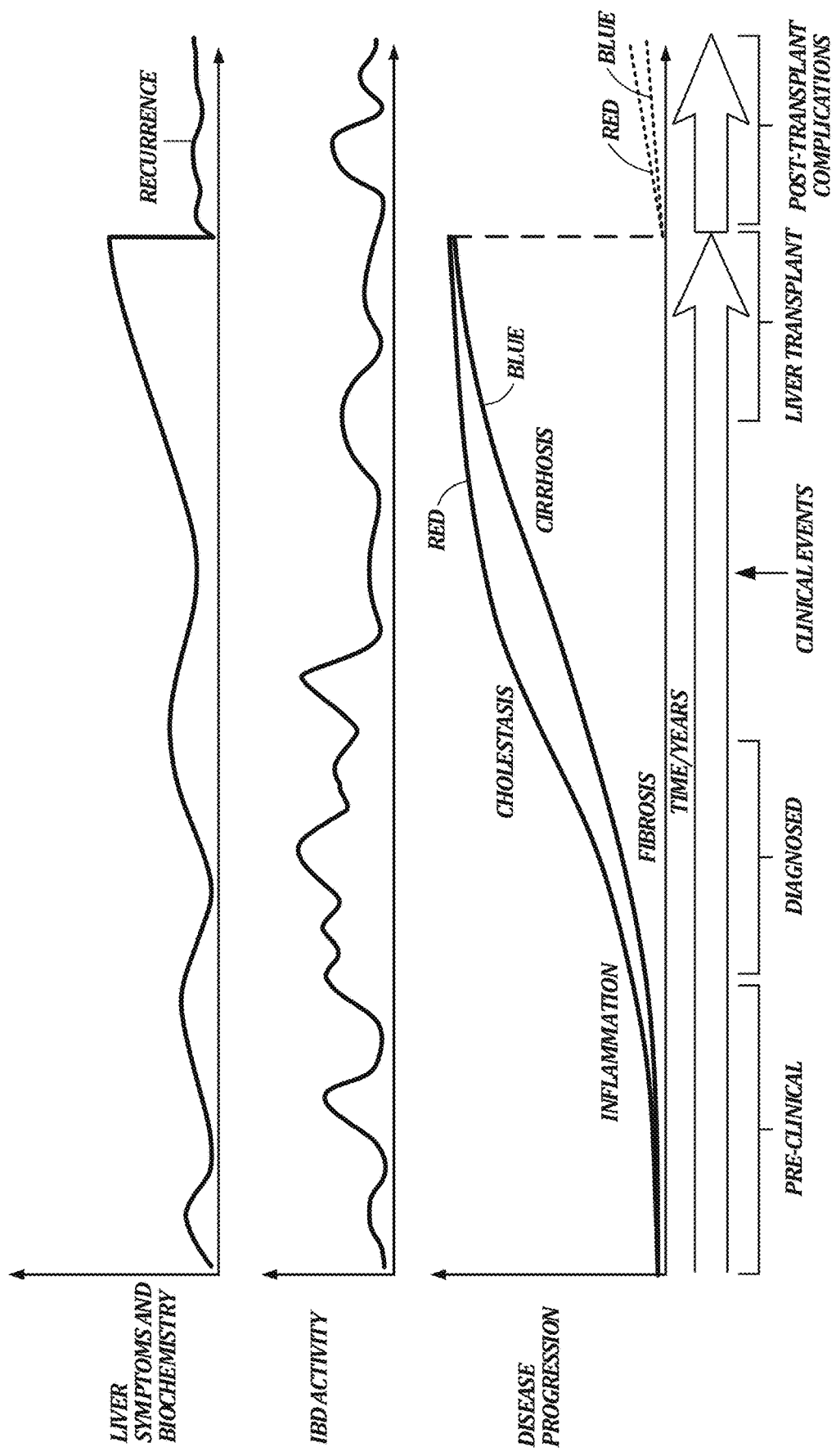
FIG. 15 is a chart of the liver symptoms and biochemistry, inflammatory bowel disease (IBD) activity, and disease progression (inflammation, cholestasis, fibrosis and cirrhosis) in relation to time in years starting from the pre-clinical stage, progressing through the diagnosed stage, the clinical events stage, the liver transplant stage and the post-transplant complications stage.

The impact of 4-MUG in drinking water on blood glucose (BG) of db/db mice, an established mouse model of type 2 diabetes was assessed. FIG. 12A graphically represents blood glucose levels in db/db mice maintained on 4-MUG in drinking water versus control water (n=5 mice per group). FIG. 12B graphically represents a blood glucose level over time in subjects following an intra-peritoneal glucose tolerance test (IPGTT). IPGTT, an evaluation of glycemic control following insulin injection, was performed by injection with 2.5 U/ml of insulin in db/db mice fed 4-MU or control chow continuously for 2 weeks. Data are representative of 2 independent experiments. *=p<0.05 for the comparison between control and 4-MUG chow. Data represent mean±SEM.

EXAMPLE 2

Delay of Onset of Diabetes

The present examples shows that compound B (Butyl-4-MUG) delays the onset of diabetes at $1/100^{th}$ the dose of 4-MU. This result is very surprising, particularly because 0.65% (approximately 10× less) 4-MU is only partially protective. Without wishing to be bound by theory, it is believed that 4-MU has low in vivo exposure and low bioavailability (~2-3%), because it is rapidly glucuronidated by first-pass metabolism, and the glucuronide (4-MUG) is rapidly excreted. Since a 4-MUG derivative is already a glucuronide, it escapes first-pass metabolism, giving it a large advantage in in vivo exposure.

In proof-of-principle studies, 12 candidate esters of 4-MU and 4 candidate esters of 4-MUG were generated and the conversion of these compounds into 4-MU in buffer containing bovin serum was examined. 8 that were readily converted into 4-MU were identified, and then two (ethyl-4-MUG, "Compound A;" and butyl-4-MUG ("Compound B")) that best inhibited HA synthesis in vitro were selected. Compounds A and B were individually administered to 8 week old DORmO mice. Compound B, butyl-4-MUG, delayed diabetes onset by one month when compared to Compound A. In contrast, mice fed Compound A, ethyl-4-MUG, developed diabetes at 12 weeks of age, at the same time as untreated DORmO mice. Notably, both pro-drugs were administered at $1/100^{th}$ of the concentration of 4-MU, suggesting that higher dosages of butyl-4-MUG may prove efficacious. These results indicate that a pro-drug strategy to increase the bioavailability of 4-MUG is feasible and pharmacologically sound.

DORmO Mice

DORmO mice were described in International Application No. PCT/US2014/050770, filed an Aug. 12, 2014 and entitled "4-Methylumbelliferone Treatment for Immune Modulation," herein incorporated by reference in its entirety.

Briefly, to determine that HA accumulates in the pancreatic islets and creates a permissive environment for autoimmune attacks during autoimmune diabetes disease progression, the DORmO double transgenic mouse model of autoimmune diabetes was used. DORmO mice predictably develop autoimmune diabetes because they are bred to have both a target antigen on their insulin producing beta-cells as well as an immune system that specifically recognizes that antigen. DORmO mice are the result of a cross between RIPmOVA mice (a strain that carries a gene specific for hen egg ovalbumin (OVA) that is only expressed on beta-cells, emulating the auto-antigen) and DO11.10 mice (a strain that carries a T-cell receptor transgene specific for OVA, emulating auto-reactive CD4+ T cells). DORmO mice spontaneously develop autoimmune insulitis starting at four weeks of age and all animals become diabetic (hyperglycemia >200 mg/dl) by 20 weeks of age (Wesley, J. D., et al., *J. Immunol.* 185, 4760-4768 (2010).

DORmO mice have spontaneous autoimmunity which closely parallels the inflammatory beta-cell destruction found in humans.

Mice

All animals were bred and maintained under specific pathogen-free conditions, with free access to food and water, in the animal facilities at Stanford University Medical School (Stanford, Calif.). B6.db/db LeptR$^{-/-}$ mice were purchased from Jackson Laboratories (JAX) as well as DO11.10 transgenic mice. The DO11.10 mice were bred with BALB/c mice expressing RIPmOva (available at the Benaroya Research Institute) to generate the DORmO double-transgenic mice. In addition C57BL/6J mice were bred in house at Stanford University School of Medicine. All animal experiments and use procedures were approved by the Institutional Animal Care & Use Committee at Stanford University School of Medicine.

Mice Diabetes Monitoring

Beginning at four weeks of age, mice were weighed weekly as well as bled via the tail vein for the determination of their blood glucose level using a Contour blood glucose meter and blood glucose monitoring strips (Bayer Healthcare). When two consecutive blood glucose readings of 250 mg/dL were recorded, animals were considered diabetic. When two consecutive blood glucose readings of 300 mg/dL were recorded, animals were euthanized.

4-MU and 4-MUG Treatment

The 4-MU (Alfa Aesar) was pressed into the mouse chow by TestDiet® and irradiated before shipment. This chow formulation delivered 250 mg/mouse/day, yielding a serum drug concentration of 640.3±17.2 nmol/L in mice, as measured by HPLC-MS. 4-MUG (ChemImpex) was distributed in the drinking water of the mice at a 5% concentration which should deliver 0.325 mg/mouse/day, yielding a serum drug concentration of 357.1±72.6 ng/mL in mice, as measured by HPLC-MS. Mice were initiated on 4-MU and 4-MUG at five, eight or twelve weeks of age, unless otherwise noted, and were maintained on this diet until they were euthanized, unless otherwise noted. For analysis of Foxp3+ regulatory T cell numbers in naïve mice, mice were treated daily with 0.5 mg of 4-MU or 1.0 mg 4-MUG in 200 μl 0.08% carboxymethylcellulose in saline by intraperitoneal (i.p.) injection.

For the in vivo part the oral delivery in the drinking water was the same as for 4-MUG. The mice receive the prodrug it in their water, water bottles were changed every other day, mice had access the water ad libitum. Compounds A and B were delivered as 0.05% in water, not 5%.

EXAMPLE 3—Synthesis of MUG Derivatives

Ethyl MUG

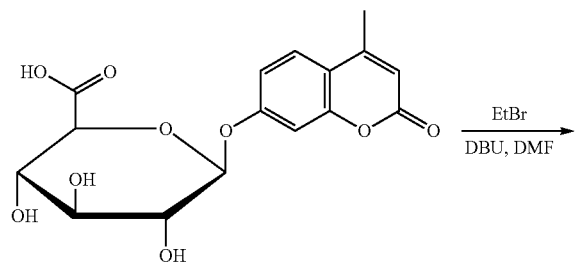

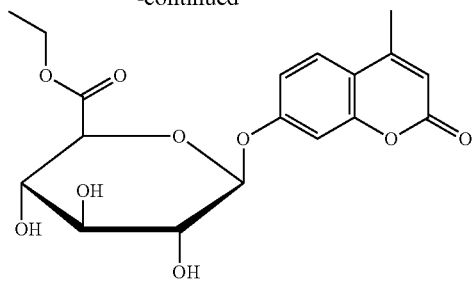

A solution of 4-methylumbelliferyl β-D-glucuronide hydrate (4-MUG) (1 g, 2.83 mmol. 1 eq.) in 10 mL of anhydrous DMF (N,N'-dimethylformamide) was stirred at 0° C. and 1,8-diazabicyclo[5.4.0]undec-7-ene (DBU) (0.46 mL, 1.1 eq) was added. This mixture was stirred for 15 minutes and then warmed up to room temperature (RT), and then stirred for additional 15 minutes. This was followed by dropwise addition of bromoethane (0.3 mL, 1.2 eq). The reaction mixture was stirred overnight at room temperature. After the reaction as completed, ethyl acetate was added to the reaction mixture to extract the product. The solution was then washed with sodium bicarbonate solution. The organic layer was dried over sodium sulfate and concentrated to obtain ethyl MUG derivate. The crude product as purified by silica gel column chromatography. Chemical Formula: $C_{16}H_{16}O_9$. Exact mass: 352.08. Molecular weight: 352.30. M/Z: 352.08 (100%), 353.08 (17.3%), 354.08 (1.8%), 354.09 (1.4%). Elemental analysis: C, 54.55; H, 4.58; 0, 40.87.

Ethyl-MUG Triacetyl

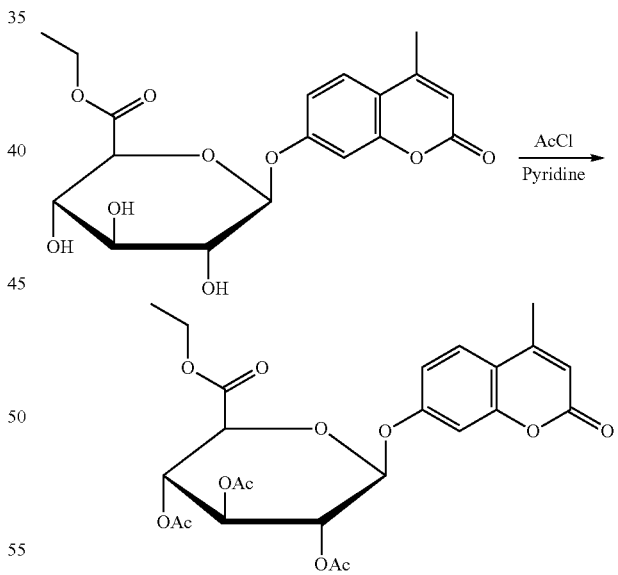

A solution of 4-methylumbelliferyl β-D-glucuronide ethyl ester (Et-MUG) (0.22 g, 0.5 mmol, 1 eq) in 10 mL of anhydrous pyridine at 0° C. was stirred for 30 minutes. To this solution acetyl chloride (0.4 mL, 10 eq.) was added dropwise. This mixture was stirred for 15 hours at 0° C. and then warmed up to room temperature, continuing the stirring overnight. The product was extracted by adding ethyl acetate and washing with bicarbonate solution. The organic layer was dried over sodium sulfate and concentrate to obtain ethyl MUG triacetyl derivative. The crude product was purified by silica gel column chromatography. Chemical Formula: $C_{24}H_{26}O_{12}$. Exact mass: 506.14. Molecular weight: 506.46. M/Z: 506.14 (100%), 507.15 (26.0%), 508.15 (2.7%), 508.15 (2.5%). Elemental analysis: C, 56.92; H, 5.17; 0, 37.91.

Butyl MUG

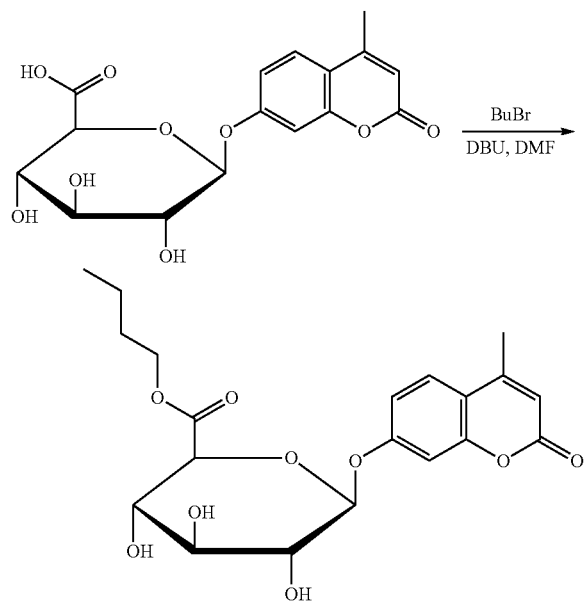

A solution of 4-methylumbelliferyl β-D-glucuronide hydrate (4-MUG) (1 g, 2.83 mmol, 1 eq) in 10 mL of anhydrous DMF was stirred at 0° C. and 1,8-diazabicyclo[5.4.0]undec-7-ene (DBU) (0.46 mL, 1.1 eq.) was added. This mixture was stirred for 15 minutes and then warmed up to room temperature, and then stirred for additional 15 minutes. This was followed by dropwise addition of 1-bromobutane (0.5 mL, 1.5 eq.). The reaction mixture was stirred for overnight at room temperature. After the reaction was completed, ethyl acetate was added to the reaction mixture to extract the product. The solution as then washed with sodium bicarbonate solution. The organic layer was dried over sodium sulfate and concentrated to obtain butyl-MUG derivative. The crude product was purified by silica gel column chromatography. Chemical Formula: $C_{20}H_{24}O_9$. Exact mass: 408.14. Molecular weight: 408.40. M/Z: 408.14 (100%), 409.15 (21.6%), 410.15 (2.2%), 410.15 (1.8%). Elemental analysis: C, 58.82; H, 5.92; 0, 35.26.

Butyl MUG Triacetyl

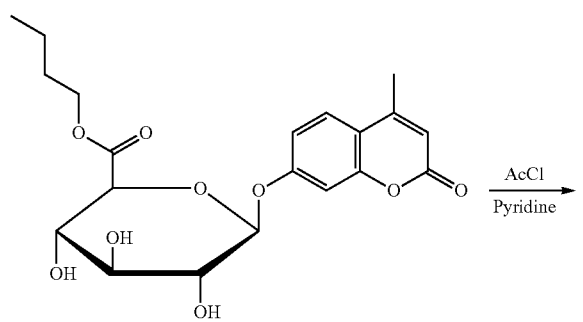

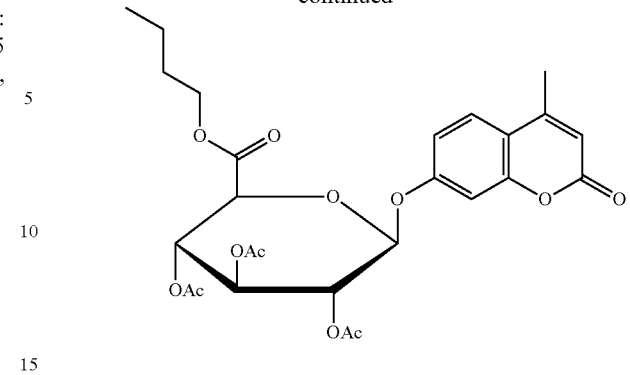

A solution of butyl-MUG (0.418 g, 1 mmol, 1 eq.) in 10 mL of anhydrous pyridine at 0° C. was stirred for 30 minutes then acetyl chloride (0.7 mL, 10 eq) was added dropwise. This mixture was stirred for 15 hours at 0° C. and then warmed up to room temperature continuing the stirring overnight. The product was extracted by adding ethyl acetate and washing with bicarbonate solution. The organic layer was dried over sodium sulfate and concentrated to obtain ethyl MUG triacetyl derivate. The crude product was purified by silica gel column chromatography. Chemical Formula: $C_{26}H_{30}O_{12}$. Exact mass: 534.17. Molecular weight: 534.51. M/Z: 534.17 (100.0%), 535.18 (28.1%), 536.18 (3.8%), 536.18 (2.5%). Elemental analysis: C, 58.42; H, 5.66; 0, 35.92.

Ethyl-MUG-Salicylate

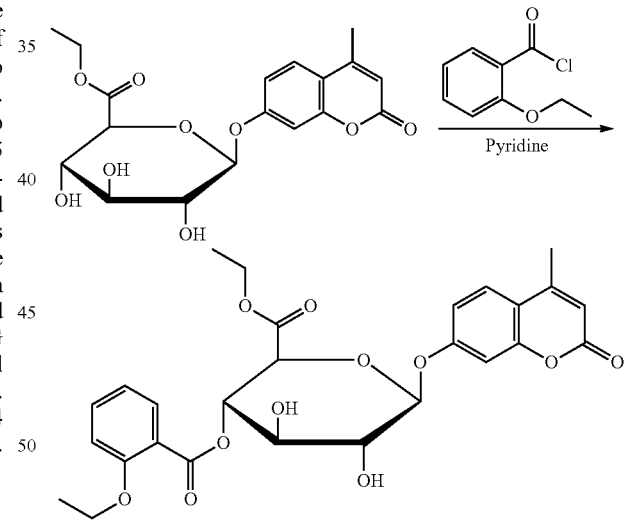

A solution of 4-methylumbelliferyl β-D-glucuronide ethyl ester (Et-MUG) (0.28 g, 0.7 mmol, 1 eq.) in 1 mL of anhydrous pyridine at 0° C. was stirred for 30 minutes. To this solution 2-ethoxybenzoyl chloride (0.5 mL, 5 eq) was added dropwise. This mixture was stirred for 15 hours at 0° C. and then warmed up to room temperature continuing the stirring overnight. The product was extracted by adding ethyl acetate and washing with bicarbonate solution. The organic layer was dried over sodium sulfate and concentrated to obtain ethyl MUG-salicylate derivate. The crude product was purified by silica gel column chromatography. Chemical Formula: $C_{27}H_{28}O_{11}$. Exact mass: 528.16. Molecular weight: 528.51. M/Z: 528.16 (100.0%), 529.17

(29.2%), 530.17 (2.7%), 530.17 (2.3%), 530.17 (1.4%). Elemental analysis: C, 61.36; H, 5.35; 0, 33.30.

EXAMPLE 4: Treatment of PSC with 4-MU

A prospective open label, single-center, pilot safety study in adults diagnosed with PSC without evidence of hepatic fibrosis is performed. Participants (n=10) are treated for 6 months with study drug (300 mg, three times a day, for months 0-3; and 600 mg, three times a day, for months 3-6). The primary outcome measure is the number of participants with adverse events as a measure of safety and tolerability. Secondary outcome measures include:

Number of participants with a qualitative improvement in the anatomy of the biliary tree as assessed by magnetic resonance cholangiopancreatography (MRCP). For example, biliary strictures may be less narrow, or there may be fewer strictures, or the volume of dilated lumen may be reduced, or there may be fewer dilations of the lumen.

Number of participants with gamma glutamyl transferase (GGT)<1.5× the upper limit of normal.

Number of participants with alkaline phosphatase (ALP) <1.5× the upper limit of normal.

HA serum levels; Treg counts.

Though safety and tolerability are nominally the primary endpoints of this trial, the safety of the parent molecule is already well-documented. Upon monitoring Treg levels, Treg induction may be documented in humans, providing first-in-human proof of concept for over-riding thesis that suppression of HA synthesis induces Treg.

No drug yet tested before this trial has been able to show a reduction in radiological measures of fibrosis, e.g., MRCP.

900 mg and 1800 mg of 4-MU are used for the trial. These doses are believed to be physiologically active.

While embodiments have been illustrated and described, it will be appreciated that various changes can be made therein without departing from the spirit and scope of the invention.

The invention claimed is:

1. A method of treating primary sclerosing cholangitis (PSC) in a subject comprising:
   selecting a subject afflicted with or at risk of developing PSC; and
   administering to the subject a therapeutically effective amount of 4-methylumbelliferone (4-MU) or an ester thereof, 4-methylumbelliferone glucuronide (4-MUG), or a compound of Formula (I):

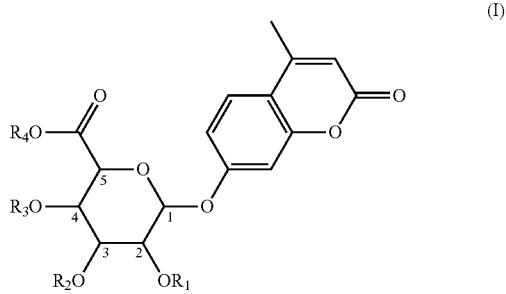

wherein
$R_1$ and $R_2$ are each independently selected from H, $C(O)-C_{1-10}$ alkyl, and $C(O)-C_{1-10}$ haloalkyl;
$R_3$ is selected from H, $C(O)-C_{1-10}$ alkyl, $C(O)-C_{1-10}$ haloalkyl, $C(O)-C_{6-10}$ aryl, and $C(O)-C_{5-10}$ heteroaryl, wherein the $C(O)-C_{1-10}$ haloalkyl, $C(O)-C_{6-10}$ aryl, and $C(O)-C_{5-10}$ heteroaryl are each optionally substituted with 1, 2, 3, or 4 substituents independently selected from halo, cyano, and nitro; and
$R_4$ is selected from $C_{2-10}$ alkyl and $C_{2-10}$ haloalkyl,
or a pharmaceutically acceptable salt thereof,
wherein progression of PSC is reduced.

2. The method of claim 1 wherein a reduction in the progression of PSC is a qualitative improvement in the anatomy of the subject's biliary tree as assessed by magnetic resonance cholangiopancreatography.

3. The method of claim 1 wherein biliary tract fibrosis is reduced or progression of biliary tract fibrosis in the subject is reduced.

4. The method of claim 3, wherein the reduction of biliary tract fibrosis or a reduction of the progression of biliary tract fibrosis is measured by an enhanced liver fibrosis score.

5. The method of claim 1, wherein a reduction of the progression of PSC is measured by a reduction in serum levels of alkaline phosphatase, aspartate aminotransferase, alanine transaminase (ALT), gamma-glutamyl transferase (GGT) or bilirubin in the subject.

6. The method of claim 1, wherein a hyaluronan (HA) level is reduced.

7. The method of claim 6, wherein the reduction of HA is measured by a reduction in serum levels of HA.

8. The method of claim 1, wherein serum levels of alkaline phosphatase aspartate aminotransferase, alanine transaminase (ALT), gamma-glutamyl transferase (GGT) or bilirubin in the subject are reduced.

9. The method of claim 1, wherein choleresis in the subject is improved.

10. The method of claim 1, wherein regulatory T cells (Tregs) in the subject are induced.

* * * * *